United States Patent [19]

McDonald, III

[11] Patent Number: 4,885,291
[45] Date of Patent: Dec. 5, 1989

[54] 1-CARBA(DETHIA)-3-CEPHEM DERIVATIVES

[75] Inventor: John H. McDonald, III, Indianapolis, Ind.

[73] Assignee: Eli Lilly and Company, Indianapolis, Ind.

[21] Appl. No.: 143,793

[22] Filed: Jan. 14, 1988

[51] Int. Cl.$^4$ ............... C07D 471/04; C07D 417/12; C07D 417/14; A61K 31/435
[52] U.S. Cl. .................................. 514/210; 540/205
[58] Field of Search ..................... 514/210; 540/205

[56] References Cited

U.S. PATENT DOCUMENTS

| | | | |
|---|---|---|---|
| 4,226,866 | 10/1980 | Christenson | 549/5 |
| 4,673,737 | 6/1987 | Evans et al. | 540/205 |
| 4,708,956 | 11/1987 | Hirata et al. | 514/210 |
| 4,760,060 | 7/1988 | Mochida | 514/210 |

FOREIGN PATENT DOCUMENTS

| | | |
|---|---|---|
| 0014476 | 8/1980 | European Pat. Off. |
| 0154253 | 11/1985 | European Pat. Off. |
| 2041923 | 9/1980 | United Kingdom |

OTHER PUBLICATIONS

Scartazzini, Helv. Chem. Acta 58, 2437(1975).
Green, "Protective (Groups in Organic Synthesis" p. 161 (1981).
EPO Search Report in applicant's corresponding EPO Application No. 89300145.3.

Primary Examiner—Mark L. Berch
Attorney, Agent, or Firm—William B. Scanlon; Leroy Whitaker

[57] ABSTRACT

7β-Acylamino-1-carba(dethia)-3-cephem-4-carboxylic acids represented by the formula

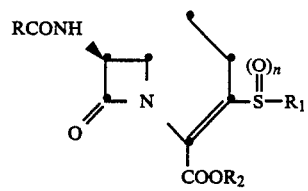

wherein n is 1 or 2;

$R_1$ is $C_1$–$C_6$ alkyl; $C_1$–$C_6$ alkyl substituted by hydroxy, $C_1$–$C_4$ alkoxy, $C_1$–$C_4$ alkylthio, trifluoromethyl, carboxy, carbamoyl, amino, $C_1$–$C_4$ alkylamino, di-($C_1$–$C_4$ alkyl)amino, halogen, cyano, phenyl, substituted phenyl as defined above; $C_2$–$C_6$ alkenyl; $C_3$–$C_7$ cycloalkyl; phenyl or substituted phenyl as defined above; or a 5- or 6-membered heterocycle selected from thienyl, furyl, pyrryl, imidazolyl, pyrazolyl, oxazolyl, isoxazolyl, thiazolyl, isothiazolyl, oxadiazolyl, thiadiazolyl, triazolyl, tetrazolyl, pyridyl, pyrimidyl, triazinyl, or pyrazinyl; the benzheterocycles, benzothienyl, benzofuryl, indolyl, benzimidazolyl, or benztriazolyl, and said 5- or 6-membered heterocycle and said benzheterocycle substituted by $C_1$–$C_4$ alkyl, halogen, hydroxy, $C_1$–$C_4$ alkoxy, amino, carboxy, cyano, or carbamoyl; and when said heterocycle or benzheterocycle contains a basic ring nitrogen, the $C_1$–$C_4$ alkyl quaternary salt thereof;

$R_2$ is hydrogen, a carboxy-protecting group, or a group forming a biologically labile ester and, when $R_2$ is hydrogen, the pharmaceutically acceptable non-toxic salts thereof; are antibiotics useful in the treatment of infectious disease.

28 Claims, No Drawings

1-CARBA(DETHIA)-3-CEPHEM DERIVATIVES

BACKGROUND OF THE INVENTION

This invention relates to synthetic β-lactam antibiotics. In particular, it relates to 7-amino and 7-substituted amino-1-carba(dethia)-3-cephem compounds substituted in the 3-position by a sulfinyl or sulfonyl group.

The class of 1-carba(dethia)-3-cephem compounds are represented by the following general formula wherein the numbering system is that employed for the arbitrary cepham nomenclature system.

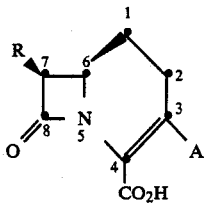

In the above formula R represents a substituted amino group and A a substituent group.

The 1-carba-3-cephem compounds have been the subject of investigation because of the need for more potent antibiotics and, particularly, antibiotics possessing activity against microorganisms resistant to the known β-lactam antibiotics.

SUMMARY OF THE INVENTION

7β-Acylamino-1-carba(dethia)-3-cephem-4-carboxylic acids and salts thereof substituted in the 3-position by an alkylsulfonyl, alkenylsulfonyl, cycloalkylsulfonyl, phenylsulfonyl, or a heterocyclic sulfonyl group and the correspondingly substituted sulfinyl groups, inhibit the growth of microorganisms pathogenic to man and animals. For example, 7β-[2-(2-aminothiazol-4yl)-2-alkoxyiminoacetylamino]-1-carba(dethia)-3-cephem-4-carboxylic acids substituted in the 3-position by an aforementioned sulfonyl or sulfinyl group possess potent activity against gram-positive and gram-negative bacteria such as *Staphylococcus, Streptococcus, Enterobacter, Salmonella* and *Hemophilus influenzae*.

The compounds of the invention are prepared by alternate routes. One route comprises the displacement of the trifluoromethylsulfonyloxy group from a 7β-acylamino-3-trifluoromethylsulfonyloxy-1-carba(dethia)-3-cephem-4-carboxylic acid ester with an alkali or alkaline earth metal salt of a sulfinic acid, for example methylsulfinic acid or phenylsulfinic acid. Alternatively, the 3-trifluoromethylsulfonyloxy-substituted compound can be reacted with an alkali metal salt of a thiol, for example methyl mercaptan or thiophenol, to form first the 3-methylthio or phenylthio compound. The latter 3-thio-substituted compounds can then be oxidized to either the corresponding sulfoxide or the sulfone.

The 1-carba-3-cephem-3-sulfone and sulfoxide compounds of the invention are useful in a method for the treatment of infectious diseases.

DETAILED DESCRIPTION

The 1-carba(dethia)-3-cephem compounds provided by this invention are represented by the following structural formula 1:

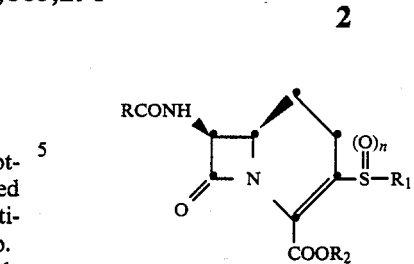

wherein R is hydrogen; $C_1$–$C_6$ alkyl; $C_1$–$C_6$ alkyl substituted by cyano, carboxy, halogen, amino, $C_1$–$C_4$ alkoxy, $C_1$–$C_4$ alkylthio, or trifluoromethylthio; a phenyl or substituted phenyl group represented by the formula

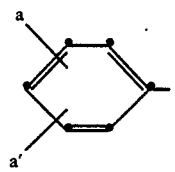

wherein a and a' independently are hydrogen, halogen, hydroxy, $C_1$–$C_4$ alkoxy, $C_1$–$C_4$ alkanoyloxy, $C_1$–$C_4$ alkyl, $C_1$–$C_4$ alkylthio, amino, $C_1$–$C_4$ alkanoylamino, $C_1$–$C_4$ alkylsulfonylamino, carboxy, carbamoyl, aminosulfonyl, hydroxymethyl, aminomethyl, or carboxymethyl;

a group represented by the formula

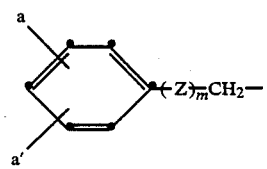

wherein a and a' have the same meanings as defined above, Z is O or S, and m is 0 or 1;

a heteroarylmethyl group represented by the formula

$R^1$—$CH_2$— wherein $R^1$ is thienyl, furyl, benzothienyl, benzofuryl, pyridyl, 4-pyridylthio, pyrimidyl, pyridazinyl, indolyl, pyrazolyl, imidazolyl, triazolyl, tetrazolyl, oxazolyl, isoxazolyl, thiazolyl, oxadiazolyl, thiadiazolyl, and such heteroaryl groups substituted by amino, hydroxy, halogen, $C_1$–$C_4$ alkyl, $C_1$–$C_4$ alkoxy, $C_1$–$C_4$ alkylsulfonylamino;

a substituted methyl group represented by the formula

wherein $R^2$ is cyclohex-1,4-dienyl, or a phenyl group or substituted phenyl group represented by the formula

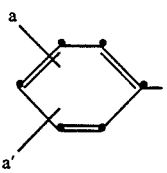

wherein a and a' have the above defined meanings, or $R^2$ is $R^1$ as defined above, and Q is hydroxy, $C_1$-$C_4$ alkanoyloxy, carboxy, sulfo, amino, sulfoamino or a substituted amino group represented by the formula

wherein $R^x$ is hydrogen or $C_1$-$C_3$ alkyl, $R^y$ is $C_1$-$C_4$ alkyl, furyl, thienyl, phenyl, halophenyl, nitrophenyl, styryl, halostyryl, nitrostyryl or a group

wherein $R^x$ is hydrogen or $C_1$-$C_3$ alkyl, and $R^z$ is hydrogen, $C_1$-$C_3$ alkylsulfonyl, $C_1$-$C_3$ alkyl, or $C_1$-$C_4$ alkanoyl; or Q is a substituted amino group represented by the formula

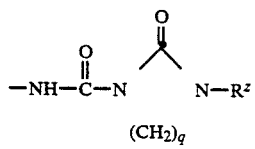

wherein $R^z$ has the same meanings as defined above and q is 2 or 3; or Q is a substituted amino group represented by the formula

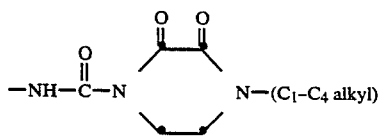

a benzamido group represented by the formula

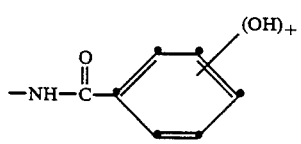

wherein t is 1 to 3;
a pyridone or hydroxy-substituted pyridone group represented by the formula

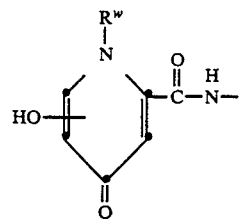

wherein $R^w$ is hydrogen or $C_1$-$C_4$ alkyl; a pyridyl group represented by the formula

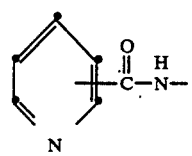

and such pyridyl group substituted by $C_1$-$C_4$ alkyl, amino, carboxy, hydroxy or halogen; an imidazoyl or pyrazolyl group represented by the formulae

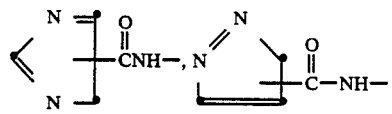

and such groups substituted by $C_1$-$C_4$ alkyl, carboxy, amino or halogen;
a benzpyridazin-4-one-3-ylcarbonylamino group represented by the formulae

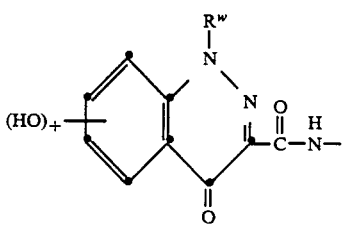

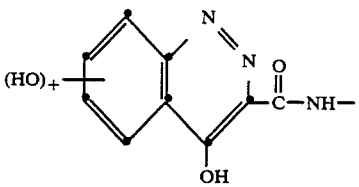

wherein $R^w$ is hydrogen or $C_1$-$C_4$ alkyl; and t is 1-3; or Q is a substituted amino group represented by the formula

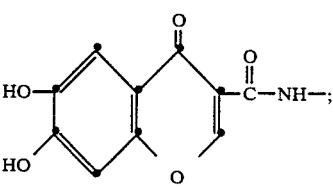

or R is a keto group or an oximino-substituted group represented by the formulae

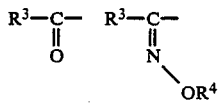

wherein R³ is R¹ or R² as defined above and R⁴ is hydrogen, $C_1$–$C_4$ alkyl, $C_1$–$C_4$ alkyl substituted by halogen or amino, a carboxy-substituted alkyl or cycloalkyl group represented by the formula

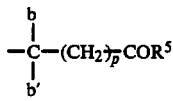

wherein b and b' independently are hydrogen, or $C_1$–$C_3$ alkyl, p is 0, 1, 2, or 3; and b and b' when taken together with the carbon to which they are bonded form a 3- to 6-membered carbocyclic ring, and R⁵ is hydroxy, $C_1$–$C_4$ alkoxy, amino, $C_1$–$C_4$ alkylamino, or di($C_1$–$C_4$ alkyl)amino;

or R⁴ is a cyclic lactam represented by the formula

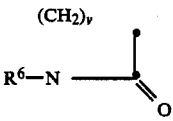

wherein v is 2, 3, or 4; and R⁶ is hydrogen or $C_1$–$C_3$ alkyl;

or R⁴ is a heteroarylmethyl group represented by the formula

wherein R¹ has the same meanings as defined hereinabove;

n is 1 or 2;

R₁ is $C_1$–$C_6$ alkyl; $C_1$–$C_6$ alkyl substituted by hydroxy, $C_1$–$C_4$ alkoxy, $C_1$–$C_4$ alkylthio, trifluoromethyl, carboxy, carbamoyl, amino, $C_1$–$C_4$ alkylamino, di-($C_1$–$C_4$ alkyl)amino, halogen, cyano, phenyl, substituted phenyl as defined above; $C_2$–$C_6$ alkenyl; $C_3$–$C_7$ cycloalkyl; phenyl or substituted phenyl as defined above; or a 5- or 6-membered heterocycle selected from thienyl, furyl, pyrryl, imidazolyl, pyrazolyl, oxazolyl, isoxazolyl, thiazolyl, isothiazolyl, oxadiazolyl, thiadiazolyl, triazolyl, tetrazolyl, pyridyl, pyrimidyl, triazinyl, or pyrazinyl, the benz heterocycle, benzothienyl, benzofuryl, indolyl, benzimidazolyl, or benztriazolyl, and said 5- or 6-membered heterocycle and said benzheterocycle substituted by $C_1$–$C_4$ alkyl, halogen, hydroxy, oxo, $C_1$–$C_4$ alkoxy, amino, carboxy, cyano, or carbamoyl; and when said heterocycle or benzheterocycle contains a basic ring nitrogen, the $C_1$–$C_4$ alkyl quaternary salt thereof.

R₂ is hydrogen, a carboxy-protecting group, or a group forming a biologically labile ester and, when R₂ is hydrogen, the pharmaceutically acceptable non-toxic salts thereof.

In the foregoing definition of formula 1, $C_1$–$C_6$ alkyl refers to the straight and branched chain alkyl groups such as methyl, ethyl, n-propyl, isopropyl, n-butyl, isobutyl, t-butyl, n-pentyl, n-hexyl, 3-methylpentyl, 3-methylbutyl, and like alkyl groups.

$C_1$–$C_6$ Alkyl substituted by cyano refers to cyanomethyl, cyanoethyl, 4-cyanobutyl, and the like; $C_1$–$C_6$ alkyl substituted by carboxy refers to such groups as carboxymethyl, 2-carboxyethyl, 2-carboxypropyl, 4-carboxybutyl, 5-carboxypentyl, and the like; $C_1$–$C_6$ alkyl substituted by halogen refers to chloromethyl, bromomethyl, 2-chloroethyl, 1-bromoethyl, 4-chlorobutyl, 4-bromopentyl, 6-chlorohexyl, 4-fluorobutyl, 3-fluoropropyl, fluoromethyl, and the like; $C_1$–$C_6$ alkyl substituted by amino refers to such groups as 2-aminoethyl, aminomethyl, 3-aminopropyl and 4-aminobutyl; $C_1$–$C_6$ alkyl substituted by $C_1$–$C_4$ alkoxy refers to methoxymethyl, 2-methoxyethyl, 2-ethoxyethyl, ethoxymethyl, 3-propoxypropyl, 3-ethoxybutyl, 4-t-butyloxybutyl, 3-methoxypentyl, 6-methoxyhexyl, and like groups; $C_1$–$C_6$ alkyl substituted by $C_1$–$C_4$-alkylthio refers to such groups as for example methylthiomethyl, 2methylthioethyl, 2-ethylthiopropyl, 4-methylthiobutyl, 5-ethylthiohexyl, 3-t-butylthiopropyl, and like groups; $C_1$–$C_6$ alkyl substituted by trifluoromethyl is exemplified by 2,2,2-trifluoroethyl, 3,3,3-trifluoropropyl, 4,4,4-trifluorobutyl, and the like; and $C_1$–$C_6$ alkyl substituted by trifluoromethylthio refers to, for example, trifluoromethylthiomethyl, 2-(trifluoromethylthio)ethyl, 2-(trifluoromethylthio)propyl, 4-(trifluoromethylthio)butyl, 5-(trifluoromethylthio)hexyl, and like $C_1$–$C_6$ alkyl substituted groups.

When in Formula (1) R is a substituted phenyl group wherein the substituent(s) are represented by a and a', examples of such groups are halophenyl such as 4-chlorophenyl, 3-bromophenyl, 2-fluorophenyl, 2,4-dichlorophenyl, and 3,5-dichlorophenyl; hydroxyphenyl such as 2-hydroxyphenyl, 3-hydroxyphenyl, 4-hydroxyphenyl, 2,4-dihydroxyphenyl, and 3,4-dihydroxyphenyl; alkoxyphenyl, such as 2,6-dimethoxyphenyl, 4-methoxyphenyl, 3-ethoxyphenyl, 3,4-dimethoxyphenyl, 4-t-butyloxyphenyl, 4-methoxy-3-ethoxyphenyl, and 4-n-propoxyphenyl; alkanoyloxyphenyl such as 2-acetoxyphenyl, 4-propionoxyphenyl, 4-formyloxyphenyl, 4-acetoxyphenyl, 3-butyryloxyphenyl, and 3-acetoxyphenyl; alkylphenyl such as 4-methylphenyl, 2-methylphenyl, 2,4-dimethylphenyl, 3-t-butylphenyl, 4-ethylphenyl, 4-ethyl-3-methylphenyl, and 3,5-dimethylphenyl; alkylthiophenyl such as 4-methylthiophenyl, 3-n-butylthiophenyl, 2-ethylthiophenyl, 3,4-dimethylthiophenyl, and 3-n-propylthiophenyl; aminophenyl such as 2-aminophenyl, 4-aminophenyl, 3,5-diaminophenyl, and 3-aminophenyl; alkanoylamino such as 2-acetylamino, 4-acetylamino, 3-propionylamino, and 4-butyrylamino; alkylsulfonylaminophenyl such a 3-methylsulfonylaminophenyl, 4-methylsulfonylaminophenyl, 3,5-(dimethylsulfonylamino)phenyl, 4-n-butylsulfonylaminophenyl, and 3-ethylsulfonylaminophenyl; carboxyphenyl such as 2-, 3-, or 4-, carboxyphenyl, 3,4-dicarboxyphenyl, and 2,4-dicarboxyphenyl; carbamoylphenyl such as 2-carbamoylphenyl, 2,4-dicarbamoylphenyl, and 4-carbamoylphenyl; hydroxymethylphenyl such as 4-hydroxymethylphenyl and 2-hydroxymethylphenyl; aminomethylphenyl such as 2-aminomethylphenyl and 3-aminomethylphenyl; and carboxymethylphenyl such as 2-carboxymethylphenyl, 4-carboxymethylphenyl, and 3,4-dicarboxymethylphenyl; and the substituted phenyl groups bearing different substituents such as 4-chloro-3-methylphenyl, 4-fluoro-3-hydroxyphenyl, 3,5-dichloro-4-hydroxyphenyl, 4-hydroxy-3-chlorophenyl, 4-hydroxy-3-methylphenyl, 4-ethyl-3-hydroxyphenyl, 4-methoxy-3-hydroxyphenyl, 4-t-butyloxy-2- hydroxyphenyl, 4-acetylamino-3-methoxyphenyl, 3-amino-4-ethylphenyl, 2-aminomethyl-4-chlorophenyl, 2-hydroxymethyl-3-methoxyphenyl, 2-hydroxymethyl-4-fluorophenyl, 2-acetoxy-4-aminophenyl, 4-acetoxy-3-methoxyphenyl, 3-isopropylthio-4-chlorophenyl, 2-methylthio-4-hydroxymethylphenyl, 4-carboxy-3-hydroxyphenyl, 4-ethoxy-3-hydroxyphenyl, 4-methylsulfonylamino-2-carboxyphenyl, 4-amino-3-chlorophenyl, and 2-carboxymethyl-4-hydroxyphenyl.

Examples of RCO— groups of Formula (1) wherein R is a group represented by the formula

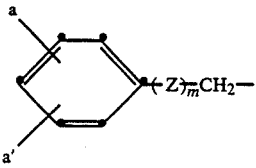

with m=0 are: phenylacetyl, 4-hydroxyphenylacetyl, 4-chlorophenylacetyl, 3,4-dichlorophenylacetyl, 4-methoxyphenylacetyl, 3-ethoxyphenylacetyl, 2-aminomethylphenylacetyl, 3-carboxyphenylacetyl, 4-acetoxyphenylacetyl, 3-aminophenylacetyl, and 4-acetylaminophenylacetyl; and with m=1 and Z=O, phenoxyacetyl, 4-chlorophenoxyacetyl, 4-fluorophenoxyacetyl, 3-aminophenoxyacetyl, 3-hydroxyphenoxyacetyl, 2-methoxyphenoxyacetyl, 2-methylthiophenoxyacetyl, 4-acetylaminophenoxyacetyl, 3,4-dimethylphenoxyacetyl, and 3-hydroxymethylphenoxyacetyl; and with m=1 and Z=S, phenylthioacetyl, 4-chlorophenylthioacetyl, 3,4-dichlorophenylthioacetyl, 2-fluorophenylthioacetyl, 3-hydroxyphenylthioacetyl, and 4-ethoxyphenylthioacetyl.

Examples of $R^1$—$CH_2CO$—groups of Formula (1) wherein $R^1$ is a heteroaryl group are: 2-thienylacetyl, 3-thienylacetyl, 2-furylacetyl, 2-benzothienylacetyl, 2-benzofurylacetyl, 3-benzothienylacetyl, indol-2-ylacetyl, 1H-tetrazol-1-ylacetyl, oxazol-2-ylacetyl, oxazol-4-ylacetyl, thiazol-4-ylacetyl, 2-aminothiazol-4-ylacetyl, 1,3,4-oxadiazol-2-ylacetyl, 1,3,4-thiadiazol-2-ylacetyl, 5-ethyl-1,3,4-thiadiazol-2-ylacetyl, pyridyl-2-acetyl, pyridyl-3-acetyl, pyridyl-4-acetyl, 4-aminopyridyl-3-acetyl, pyrimidin-2-ylacetyl, pyrimidin-4-ylacetyl, 2-aminopyrimidin-4-ylacetyl, 4-aminopyrimidin-2-ylacetyl, pyridazin-3-acetyl, pyridazin-4-acetyl, pyrazol-3-ylacetyl, 3-methylpyrazol-1-ylacetyl, imidazol-2-ylacetyl, imidazol-1-ylacetyl, 2-aminoimidazol-3-ylacetyl, 3-chloroimidazol-4-ylacetyl, and like heteroaryl groups optionally substituted by amino, $C_1$-$C_4$ alkylsulfonylamino, hydroxy, halo, $C_1$-$C_4$ alkyl or $C_1$-$C_4$-alkoxy groups.

Examples of RCO— groups of Formula (1) compounds wherein R is a substituted methyl group represented by the formula $R^2$—CH(Q)— and Q is amino, carboxy, hydroxy, or sulfo, are 2-carboxy-2-phenylacetyl, 2-carboxy-2-(4-hydroxyphenyl)acetyl, 2-amino-2-phenylacetyl, 2-amino-2-(4-hydroxyphenyl)acetyl, 2-amino-2-(3-chloro-4-hydroxyphenyl)acetyl, 2-amino-2-(cyclohex-1,4-dien-1yl)acetyl, 2-hydroxy-2-phenylacetyl, 2-formyloxy-2-phenylacetyl, 2-sulfo-2-phenylacetyl, 2-sulfo-2-(4-methylphenyl)acetyl, and 2-acetoxy-2-(3-hydroxyphenyl)acetyl, 2-amino-2-(2-thienyl)acetyl, 2-sulfoamino-2-phenylacetyl, 2-sulfoamino-2-(4-hydroxyphenyl)acetyl, 2-sulfoamino-2-(2-aminothiazol-4-yl)acetyl, 2-amino-2-(benzothien-2-yl)acetyl, 2-amino-2-(3-methylsulfonylphenyl)acetyl, 2-sulfoamino-2-(1,4-cyclohexadien)acetyl, 2-amino-2-(3-benzothienyl)acetyl, 2-amino-2-(1H-tetrazol-1-yl)acetyl, 2-hydroxy-2-(1,3,4-thiadiazol-2-yl)acetyl, 2-amino-2-(2-aminothiazol-4-yl)acetyl, 2-carboxy-2-(2-thienyl)acetyl, 2-carboxy-2-(benzothien-2-yl)acetyl, and 2-hydroxy-2-(benzofur-2-yl)acetyl; and when Q is a substituted amino group represented by the formula

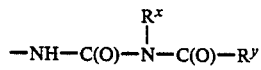

examples of such acyl groups are 2-(N-methyl-N-benzoylcarbamoylamino)-2-phenylacetyl, 2-(N-methyl-N-cinnamoylcarbamoylamino)-2-(2-furyl)acetyl, 2-(N,N-dimethylcarbamoylureido)-2-(4-chlorophenyl)acetyl, 2-[N-methyl-N-(2-chlorocinnamoyl)carbamoylamino]-2-(2-thienyl)acetyl, and 2-(N-ethyl-N-acetylcarbamoylamino)-2-(4-hydroxyphenyl)acetyl; and when Q is a substituted amino group represented by the formula

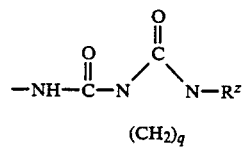

examples of acyl group R(CO—) are 2-[(3-methylimidazolidin-2-one-1-yl)carbonylamino]-2-phenylacetyl, 2-[(3-acetylimidazolidin-2-one-1-yl)carbonylamino]-2-phenylacetyl, 2-[(3-methylsulfonylimidazolidin-2-one-1-yl)-2-(2-thienyl)acetyl, and 2-[(3-acetylhexahydropyrimidin-2-one-1-yl)carbonylamino]-2-phenylacetyl; and when Q is a hydroxy-substituted benzamido group represented by the formula

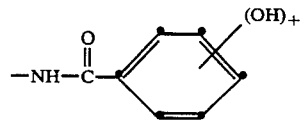

examples of such acyl groups are 2-(2,4-dihydroxybenzamido)-2-phenylacetyl, 2-(4-hydroxybenzamido)-2-(4-hydroxyphenyl)acetyl, 2-(3,4-dihydroxybenzamido)-2-(2-aminothiazol-4-yl)acetyl, 2-(3,5-dihydroxybenzamido)-2-(3-thienyl)acetyl, and 2-(2-hydroxybenzamido)-2-(2-benzofuryl)acetyl.

When Q is an hydroxy-substituted pyridinecarbonylamino group, examples include e.g., 2-hydroxypyridin-4-one-6-ylcarbonylamino and 3-hydroxypyridin-4-one-6-ylcarbonylamino. When Q is a pyridylcarbonylamino group examples are e.g., pyridin-3-ylcarbonylamino, 4-aminopyridin-3-ylcarbonylamino, 5-chloropyridin-2-ylcarbonylamino, 3-carboxypyridin-4-ylcarbonylamino, and 4-aminopyridinio-2-ylcarbonylamino. When Q is an imidazole or pyrazole group as defined above examples include e.g., 2-aminoimidazol-4-ylcarbonylamino, 5-carboxy-2-methylimidazol-4-ylcarbonylamino, 5-carboxypyrazol-3-ylcarbonylamino, 3-aminopyrazol-4-ylcarbonylamino and 4-hydroxypyrazol-5-ylcarbonylamino. When Q is a benzpyridazin-4-one-3-ylcarbonylamino group, examples of Q are represented by the formulae (including the tautomeric form when $R^3$=H)

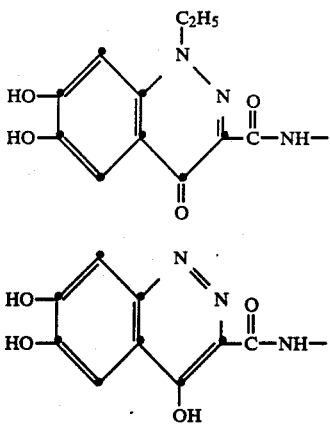

Examples of RCO acyl groups of the compounds represented by formula 1 when R is a keto group or an oximino-substituted group represented by the formulae

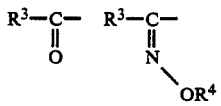

are the keto groups 2-oxo-2-phenylacetyl, 2-oxo-2-(2-thienyl)acetyl, 2-oxo-2-(2-aminothiazol-4-yl)acetyl; and oximino-substituted groups 2-phenyl-2-methoxyiminoacetyl, 2-(2-thienyl)-2-ethoxyiminoacetyl, 2-(2-furyl)-2-methoxyiminoacetyl, 2-(2-benzothienyl)-2-carboxymethoxyiminoacetyl, 2-(2-thienyl)-2-(2-carboxyethoxy)iminoacetyl, 2-(5-amino-1,2,4-thiadiazol-3-yl)-2-methoxyiminoacetyl, 2-(2-aminothiazol-4-yl)-2-methoxyiminoacetyl, 2-(2-chlorothiazol-4-yl)-2-methoxyiminoacetyl, 2-(2-aminothiazol-4-yl)-2-(2-carboxyprop-2-yl)oxyiminoacetyl, 2-(2-aminothiazol-4-yl)-2-(2-carbamoylprop-2-yl)oxyiminoacetyl, 2-(5-amino-1,3,4-thiadiazol-2-yl)-2-methoxyiminoacetyl, 2-(2-aminothiazol-4-yl)-2-(pyrrolidin-2-one-yl)oxyiminoacetyl, 2-(2-aminothiazol-4-yl)-2-(1-methylpyrrolidin-2-one-3-yl)oxyiminoacetyl, 2-phenyl-2-(pyrrolidin-2-one-3-yl)oxyiminoacetyl, 2-(2-aminooxazol-4-yl)-2-(1-ethyl-pyrrolidin-2-one-3-yl)oxyiminoacetyl, 2-(2-aminothiazol-4-yl)-2-(1-ethylpiperidin-2-one-3-yl)-2-oxyiminoacetyl, and 2-(2-furyl)-2-(pyrrolidin-2-one-3-yl)oxyiminoacetyl.

With respect to the term $R_1$ as defined for formula 1, $C_1-C_6$ refers to the same straight or branched chained groups as exemplified above for the term R. Substituted $C_1-C_6$ alkyl refers to the groups exemplified hereinabove for the term R and, in addition, to hydroxy-$C_1-C_6$ alkyl such as hydroxymethyl, hydroxyethyl, hydroxypropyl, 3-hydroxyphenyl, hydroxyhexyl, and the like; to trifluoromethyl-$C_1-C_6$ alkyl, e.g., trifluoromethyl, 2,2,2-trifluoroethyl, 2-trifluoromethylpropyl, 4,4,4-trifluorobutyl, and the like; to carbamoyl-$C_1-C_6$ alkyl such as, e.g., 2-carbamoylethyl, 3-carbamoylpropyl, carbamoylmethyl, 4-carbamoylpentyl, and the like; to $C_1-C_4$ alkylamino and di-($C_1-C_4$ alkyl)amino such as, e.g., methylaminomethyl, diethylaminomethyl, diethylaminoethyl, 2-(methylethylamino)propyl, di-(n-butyl)aminomethyl, 3-dimethylaminopentyl, and the like; to phenyl-$C_1-C_6$ alkyl such as, e.g., benzyl, 2-phenylethyl, 3-phenylpropyl, 1-phenylethyl, 6-phenylhexyl, and the like; and to such phenyl-$C_1-C_6$ alkyl groups wherein the phenyl group is substituted such as, e.g., with the substituted phenyl groups exemplified hereinabove.

Examples of $C_2-C_6$ alkenyl groups represented by $R_1$ are vinyl, allyl, butenyl or hexenyl; cycloalkyl groups represented by $R_1$ include, for example cyclopropyl, cyclobutyl, cyclopentyl, and cyclohexyl. When $R_1$ represents substituted phenyl, such groups are exemplified by the substituted phenyl groups mentioned hereinabove for the term R. Examples of heterocyclic sulfoxides and sulfones represented by the term

are 2-thienylsulfonyl, 2-thienylsulfoxide, 3-thienylsulfonyl, 2-furylsulfoxide, 2-furylsulfonyl, 2-pyrrylsulfonyl, 1-methyl-2-pyrrylsulfonyl, 2-imidazolylsulfoxide, 2-imidazolylsulfonyl, 1-ethyl-2-imidazolylsulfonyl, 3-pyrazolylsulfoxide, 2-oxazolylsulfonyl, 2-thiazolylsulfonyl, 2-(s-triazolyl)sulfinyl, 2-(1,3,4-thiadiazolyl)sulfoxide, 2-(1,3,4-oxadiazolyl)sulfonyl, 5-tetrazolylsulfonyl, 3-pyridylsulfonyl, 4-pyridylsulfonyl, 2-pyrimidylsulfoxide, 2-pyrimidylsulfonyl, 2-(5-oxo-6-hydroxy-1,3,4-triazinyl)sulfonyl, 2-(1-methyl-5-oxo-6-hydroxy-1,3,4-triazinyl)sulfonyl, 2-pyrazinylsulfoxide, 2-pyrazinylsulfonyl, 2-benzothienylsulfonyl, 2-benzofurylsulfonyl, 3-(1-methylindolyl)sulfonyl, 2-benzimidazolylsulfonyl, and said heterocyclic sulfoxides and sulfones substituted by $C_1-C_4$ alkyl, halogen, hydroxy, oxo, $C_1-C_4$ alkoxy, amino, carboxy, cyano, or carbamoyl; and when said heterocycle contains a basic ring nitrogen, the $C_1$-$C_4$ alkyl quaternary salts thereof formed with alkyl iodides, bromides and chlorides, such as, e.g., 1-methyl-2-pyrrylsulfonyl methiodide, 4-pyridylsulfonyl methiodide, 4-pyridylsulfonyl methyl bromide, 2-pyrimidylsulfoxide ethiodide, 2-pyrimidylsulfonyl methiodide, and like quaternary salts.

The term "carboxy-protecting group" refers to conventional groups commonly used in the β-lactam and peptide arts to protect or block the acidic carboxy group while a reaction is carried out at another site in the molecule. Examples of such protecting groups are t-butyl, isoamyl, allyl, 2-iodoethyl, 2,2,2-trichloroethyl, benzyl, 4-methoxybenzyl, 4-nitrobenzyl, diphenylmethyl, 4-methoxydiphenylmethyl, phenacyl, and silyl ester groups such as trialkylsilyl, e.g. trimethylsilyl, and dimethyl-t-butylsilyl, trialkylsilylethyl groups, e.g. 2-(trimethylsilyl)ethyl and 2-(diethyl-t-butylsilyl)ethyl.

The 1-carbacephalosporins provided by the invention form salts with suitable bases, in particular, the pharmaceutically acceptable, non-toxic salts. The C-4 carboxy group of the 1-carbacephalosporin can form salts with the alkali and alkaline earth metal hydroxides, carbonates and bicarbonates. Examples of such pharmaceutically acceptable salts are the sodium, potassium, calcium, and magnesium salts. Salts also may be formed with amines such as dibenzylamine, cyclohexylamine, triethylamine, ethanolamine, di-ethanolamine, and like amines. Likewise, when the 1-carbacephalosporin is substituted by two or more carboxy groups, di- and tri-salts are obtained by conventional salt-forming methods.

1-Carbacephalosporin compounds represented by the formula 1 which bear an amino group substituent either in the 7-position side chain or in the 3-position substituent also form salts with suitable acids to provide the antibiotics as pharmaceutically acceptable salts. Examples of suitable acids are hydrochloric, hydrobromic, sulfuric, and phosphoric.

Biologically labile ester groups represented by the term $R_2$ (formula 1) can enhance the absorbability of the antibiotic compound in comparison to the free acid or salt form ($R_2$=H). Accordingly, they can be useful forms of the compounds in formulations for oral administration. Examples of biologically labile ester groups represented by $R_2$ are an acyloxyalkyl group represented by the formula

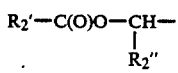

wherein $R_2'$ is $C_1$–$C_4$ alkyl and $R_2''$ is hydrogen or $C_1$–$C_4$ alkyl; an alkyl ether group represented by the formula ($C_1$–$C_4$ alkyl)—O—CH$_2$CH$_2$—O—CH$_2$—;

phthalidyl, indanyl, or the cyclocarbonate group represented by the formula

Examples of acyloxyalkyl ester groups are acetoxymethyl, propionoxymethyl, pivaloyloxymethyl, 1-acetoxyethyl ($R_2'$=CH$_3$, $R_2\Delta$=CH$_3$), 1-acetoxypropyl, and 1-propionoxybutyl. Examples of the alkyl ether labile esters are β-methoxyethoxymethyl, β-t-butyloxyethoxymethyl, and like ethers.

Preferred compounds of the invention are represented by formula 1 wherein R is an oximino-substituted group represented by the formula

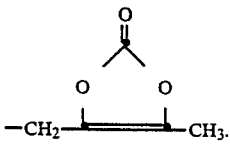

wherein $R^3$ and $R^4$ have the same meanings as defined for formula 1. Especially preferred oximino-substituted compounds are those wherein the oximino group has the syn (z) configuration.

Preferred oximino-substituted compounds are represented by formula 1 wherein $R^3$ is phenyl or substituted phenyl as defined hereinabove, thienyl, furyl, oxazolyl, thiadiazolyl, or thiazolyl, and such heterocycles substituted by amino, hydroxy, halogen, $C_1$–$C_4$ alkyl, $C_1$–$C_4$ alkoxy, or $C_1$–$C_4$ alkylsulfonylamino; $R^4$ is $C_1$–$C_4$ alkyl or a carboxy-substituted alkyl or cycloalkyl group; $R_1$ is $C_1$–$C_6$ alkyl and n is 2.

Particularly preferred compounds of the invention are represented by the following formula

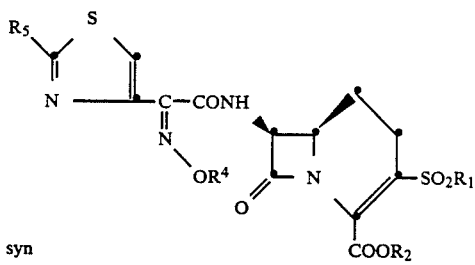

wherein $R_5$ is amino or protected amino, $R^4$ is $C_1$–$C_4$ alkyl, preferably methyl, or a carboxy or protected carboxy-substituted alkyl group, $R_1$ is $C_1$–$C_6$ alkyl, $C_1$–$C_6$ substituted alkyl, $C_3$–$C_7$ cycloalkyl, phenyl, or substituted phenyl as defined hereinabove; and $R_2$ is hydrogen or a carboxy-protecting group, and when $R_2$ is hydrogen, the pharmaceutically acceptable non-toxic salts thereof. The preferred compounds represented by foregoing formula include the antibiotic compounds themselves wherein $R_5$ is amino and $R_2$ is hydrogen or a pharmaceutically acceptable salt thereof. Also included in the above formula are the immediate precursors to the antibiotic compounds and are the compounds where the amino group $R_5$ is a protected amino group as defined hereinafter, and $R_2$ is a carboxy-protecting group as defined hereinabove.

Examples of the antibiotic compounds represented by the above formula include the following:

7β-[2-(2-aminothiazol-4-yl)-2-(Z)-methoxyiminoacetamido]-3-methylsulfonyl-1-carba(dethia)-3-cephem-4-carboxylic acid, 7β-[2-(2-aminothiazol-4-yl)-2-(Z)-methoxyiminoacetamido]-3-isopropylsulfonyl-1-carba(dethia)-3-cephem-4-carboxylic acid, 7β-[2-(2-aminothiazol-4-yl)-2-(Z)-(2-carboxyprop-2-yl)oxyiminoacetamido]-3-ethylsulfonyl-1-carba(dethia)-3-cephem-4-carboxylic acid, 7β-[2-(2-aminothiazol-4-yl)-2-(Z)-methoxyiminoacetamido]-3-phenylsulfonyl-1-carba(dethia)-3-cephem-4-carboxylic acid, 7β-[2-(2-aminothiazol-4-yl)-2-(Z)-methoxyiminoacetamido]-3-(4-hydroxyphenylsulfonyl)-1-carba(dethia)-3-cephem-4-carboxylic acid, and the pharmaceutically acceptable non-toxic salts thereof.

Examples of amino-protected and carboxy-protected precursors of the above-preferred antibiotic compounds are:

allyl 7β-[2-(2-tritylaminothiazol-4-yl)-2-(Z)-methoxyiminoacetamido]-3-methylsulfonyl-1-carba(dethia)-3-cephem-4-carboxylate, 4-methoxybenzyl 7β-[2-(2-t-butyloxycarbonylaminothiazol-4-yl)-2-(Z)-ethoxyiminoacetamido]-3-phenylsulfonyl-1-carba(dethia)-3-cephem-4-carboxylate, diphenylmethyl 7β-[2-(2-benzyloxycarbonylaminothiazol-4-yl)-2-(Z)-t-butyloxycarbonylmethoxyiminoacetamido]-3-(4-hydroxyphenylsulfonyl)-1-carba(dethia)-3-cephem-4-carboxylate, and p-nitrobenzyl 7β-[2-(2-tritylaminothiazol-4-yl)-2-(Z)-(2-carbamoylethoxy)iminoacetamido)-3-benzylsulfonyl-1-carba(dethia)-3-cephem-4-carboxylate.

As was mentioned hereinabove, the compounds of formula 1 wherein $R_2$ is hydrogen and the pharmaceutically acceptable non-toxic salts thereof inhibit the growth of microorganisms pathogenic to man and animals. For example, in standard in vitro tests, the compounds exhibit significant antibacterial activity against *Staphylococci, Streptococci, Haemophilus influenzae, Escherichia coli, Klebsiella, Enterobacter, Salmonella, Shigella, Proteus, Serratia marcescens,* as well as other pathogenic organisms.

The compounds represented by formula 1 wherein n is 2 are prepared with the corresponding 3-trifluoromethylsulfonyloxy-1-carba(dethia)-3-cephem-4-carboxylic acid in the esterified form by reaction with the sulfinate salt, $R_1SO_2^-A^+$, followed by deesterification and removal of any amino or carboxy-protecting groups present in the 7-position side chain. The foregoing preparation is illustrated in the following reaction scheme.

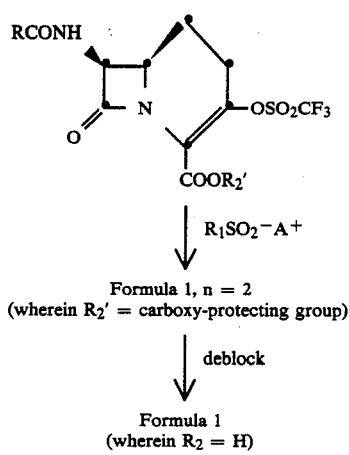

Formula 1, n = 2
(wherein $R_2'$ = carboxy-protecting group)

↓ deblock

Formula 1
(wherein $R_2$ = H)

In the above reaction scheme, R and $R_1$ have the same meanings as defined hereinabove for formula 1, $R_2'$ is a carboxy-protecting group, and $A^+$ represents a cation, for example an alkali metal cation such as lithium, sodium, or potassium. The sulfinate salt may also be formed with a divalent cation such as an alkaline earth cation, for example magnesium or calcium, in which case the sulfinate salt is represented by the formula $(R_1SO_2)_2^{--}A^{++}$.

The 3-trifluoromethylsulfonyloxy-3-cephem starting material (triflate) is obtained as described by Evans et al., in U.S. Pat. No. 4,665,171. The sulfinate salts are prepared by known methods or are commercially available.

The compounds represented by formula 1 wherein n is 1 (sulfoxides) are obtained by the reaction of the triflate starting material in esterified form with the thiol $R_1SH$ or an alkali metal salt or a trialkylammonium salt thereof, for example $R_1S^-A^+$. The thiol or the salt form thereof displaces the triflate ester to form the corresponding 3-$R_1$sulfide-3-cephem ester. The sulfide is then oxidized to the sulfoxide form with a peracid such as m-chloroperbenzoic acid or peracetic acid. The foregoing preparation of the 3-sulfoxide-3-cephem compounds represented by formula 1 is illustrated in the following reaction scheme.

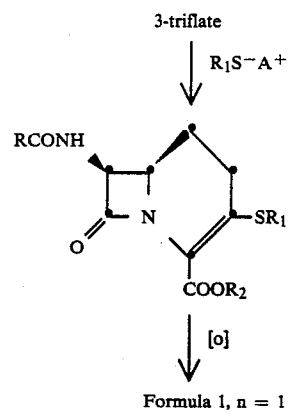

Formula 1, n = 1

In carrying out the preparation of the 3-sulfonyl compound of formula 1 wherein n is 2, the triflate ester is dissolved in an inert organic solvent such as acetonitrile or dimethylformamide and the sulfonate salt is added to the solution. The displacement occurs readily at a temperature between about 15° C. and about 65° C. The course of the reaction can be followed via thin layer chromatography by removing a small aliquot from the reaction mixture from time to time for chromatography. The 3-sulfonyl ester product is recovered from the reaction product mixture by conventional means. For example, the reaction product mixture is diluted with an organic solvent such as ethyl acetate or methylene chloride and the solution is washed with dilute acid, for example 1N hydrochloric acid and with water, is dried and chromatographed over silica gel to provide the product. Alternatively, the reaction mixture may be evaporated to dryness and the residue taken up in an organic solvent such as ethyl acetate and purified as before by chromatography over silica gel.

The preparation of a 3-sulfoxide ester of formula 1 wherein n is 1 is likewise carried out in an inert organic solvent such as acetonitrile, tetrahydrofuran, or methylene chloride by adding a solution of an alkali metal thiolate, $R_1S^-A^+$, or the thiol $R_1SH$ and an organic base, e.g., a tertiary amine such as triethylamine or diisopropylethylamine, in a mixture of a water miscible organic solvent and water to the solution of the triflate ester in the organic solvent. The mixture is stirred at the reaction temperature range, preferably at about 20° C. to about 30° C. to form the 3-thio ester as shown above in the reaction scheme. The thio ester is isolated by conventional means, for example by extraction, and is then oxidized in an inert solvent with a peracid, preferably m-chloroperbenzoic acid, to form the sulfoxide. It is also possible to convert the 3-sulfide ester to the sulfone (formula 1, n=2) by oxidation with a stronger oxidizing agent such as, for example sodium persulfate or an excess amount of peracetic acid.

Following the preparation of the compound of formula 1 wherein $R_2$ is a carboxy-protecting group, the product sulfone or sulfoxide ester is deesterified to provide the antibiotic free acid (formula 1, $R_2$=H). Likewise, any protected amino groups or protected carboxy groups occurring elsewhere in the molecule, for example in the 7-position side chain, are removed to provide the free amino and free carboxy-substituted compounds. The protecting groups employed in this invention are conventional amino and carboxy-protecting groups as described herein.

Amino-protecting groups which can be used in the preparation of the compounds represented by formula 1 to protect or block any amino group in the 7-position side chain or the 3-position substituent include the enamines formed with the amino group and a keto ester such as methyl or ethyl acetoacetate; the trityl group; a urethane-forming group represented by the formula

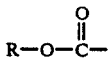

wherein R is $C_1$–$C_6$ alkyl, $C_1$–$C_6$ alkyl substituted by halogen, $C_3$–$C_6$ alkenyl, $C_3$–$C_6$ cycloalkyl, bicycloalkyl, phenyl, nitrophenyl, or diphenylmethyl, such as, e.g., methoxycarebonyl, ethoxycarbonyl, t-tutyloxycarbonyl, amyloxycarbonyl, trichloroethoxycarbonyl, allyloxycarbonyl, cyclopentyloxycarbonyl, cyclohexyloxycarbonyl, bicycloheptyloxycarbonyl, adamantyloxycarbonyl, benzyloxycarbonyl, p-nitrobenzyloxycarbonyl, diphenylmethoxycarbonyl, and the like; a diacyl-protecting group such as, e.g., phythaloyl; and the so-called "Ox" group which, with the amino nitrogen atom, forms the 4,5-diphenyl-4-oxazolin-2-one-3-yl group.

A further aspect of the invention provides intermediates represented by formula 2

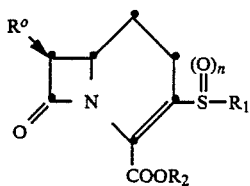

wherein $R°$ is amino or protected amino; and $R_1$, $R_2$, and n have the same meanings as defined for formula 1.

The compound of formula 2 is obtained with the corresponding 7-amino-protected-3-trifluoromethylsulfonyloxy 1-carba compound by the method described hereinabove for the preparation of 7-acylamino compound represented by formula 1. Following the displacement of the 3-triflate groups with a thiol and oxidation with a peracid, the 3-sulfoxide substituted compound (formula 2, n=1), or following displacement of the 3-triflate with $R_1SO_2^+A^-$, the 3-sulfonyl substituted compound, is deprotected. The free 7-amino group is then acylated with the desired carboxylic acid RCOOH to provide the compound represented by formula 1 wherein $R_2$ is a protected carboxy group. Deesterification of the carboxy-protecting group provides the antibiotic compound (formula 1, $R_2$=H or salt).

The acylation of 2 wherein $R°$ is amino is carried out by conventional N-acylation methods. For example, the acid RCOOH can be converted to an active derivative such as the acid chloride, acid azide or an anhydride and the active derivative used in the acylation. N-Acylation methods commonly used in the acylation of the penicillin (6-APA) and cephalosporin nuclei (7-ACA, 7-ADCA) are applicable in the acylation of 2 ($R°$=amino).

Alternatively, a compound represented by formula 2 wherein $R°$ is amino and $R_2$ is a carboxy-protecting group is obtained by the N-deacylation of a compound represented by formula 1 wherein $R_2$ is a carboxy-protecting group. The N-deacylation is carried out by formation of the imido halide derivative of the 7-amido function with a phosphorus halide such as $PCl_5$. The imido halide is converted to the imino ether by reaction with an alcohol, and the imino ether hydrolyzed to the 7-amino-1-carba ester 2.

Examples of 7-amino-1-carba nucleus compounds (2) are:

7-amino-3-methylsulfonyl-1-carba(dethia)-3-cephem-4-carboxylic acid, 7-amino-3-ethylsulfonyl-1-carba(dethia)-3-cephem-4-carboxylic acid, p-nitrobenzyl 7-amino-3-isopropylsulfonyl-1-carba(dethia)-3-cephem-4carboxylate, diphenylmethyl 7-amino-3-benzylsulfonyl-1-carba(dethia)-3-cephem-4-carboxylate, p-methoxybenzyl 7-amino-3-(2-thienylsulfonyl)-1-carba(dethia)-3-cephem-4-carboxylate, allyl 7-amino-3-(3-pyridylsulfonyl)-1-carba(dethia-3-cephem-4-carboxylate, and 7-amino-3-methylthio-1-carba(dethia)-3-cephem-4-carboxylic acid sulfoxide.

The 7-amino compounds (formula 2, $R°=NH_2$) form salts with common acids such as the mineral acids, e.g., hydrochloric acid, hydrobromic acid, sulfuric acid, and phosphoric acid, and the organo sulfonic acids such as methanesulfonic acid, n-butanesulfonic acid, benzenesulfonic acid, p-toluenesulfonic acid, and napthalenesulfonic acid. Such salts are useful for isolating and purifying the 7-amino free acids and esters thereof.

The compounds represented by formula 1 wherein $R_2$ is a biologically labile ester group are obtained with the salt form of a compound of formula 1 and a reactive derivative of the biologically labile ester moiety. For example, a compound of formula 1 as the sodium salt is reacted with an acyloxyalkyl halide, such as the chloride, bromide, or iodide, to provide the active ester. For example, pivaloyloxymethyl bromide is reacted with the sodium salt of the antibiotic to provide the pivaloyloxymethyl active ester. Likewise, 1-acetoxyethyl bromide is reacted with the sodium salt of the antibiotic to provide the 1-acetoxyethyl active ester. In a similar manner, an alkoxyethoxymethyl bromide is reacted with the sodium salt of an antibiotic of formula 1 to provide the alkyl ether active ester form of the compound. For example, ethoxyethoxymethyl bromide is reacted with the sodium salt form of the antibiotic to provide the ethoxyethoxymethyl active ester of the antibiotic. In a similar fashion, phthalidyl, indanyl or the cyclocarbonate active esters are prepared.

In a further aspect of this invention there is provided a method for the treatment or control of bacterial infections in man and animals which comprises administering between about 50 mg and about 2000 mg of a compound of formula 1 wherein $R_2$ is other than a carboxy-protecting group. The compounds of the invention or a pharmaceutically acceptable salt thereof can be administered parenterally, for example intramuscularly, subcutaneously, or intravenously, in a suitable formulation. The biologically active ester form of the compound of formula 1 can be administered orally, for example in standard oral formulations such as capsules, tablets, and suspensions. The biologically labile ester form of the antibiotic may also be administered parenterally. For parenteral administration, the antibiotic is formulated prior to administration in a suitable physiological diluent, for example Water for Injection, 5% glucose, Ringer's solution, or physiological saline. The compounds may be administered in a single dose or in multiple doses throughout the day, for example bid., tid., or quid. The number of doses and the amount of the individual dose may vary depending upon such conditions as the potency of the individual antibiotic, the particular organism or organisms causing the infection, the severity of the infection, the general health and well being of the patient, and the tolerance of the individual patient to the antibiotic. The antibiotic may also be administered by iv infusion whereby the host is treated with the antibiotic by slow intravenous infusion over 1-2 hours or longer.

This invention also provides antibiotic formulations comprising an antibacterially effective amount of an antibiotic compound of formula 1, wherein $R_2$ is other than a carboxy-protecting group, and a pharmaceutically acceptable carrier. Pharmaceutically acceptable carriers include for parenteral administration Water for Injection, 5% glucose, physiological saline, or other physiologically suitable fluid commonly employed for the parenteral administration of antibiotics. For oral administration of the bilogically labile esters, pharmaceutical carriers include gelatin capsules and tablet forms of the antibiotic comprising a suitable binding agent, lubricant, coloring agent, or flavoring agent. For example, such tablets may contain talc, magnesium stearate, a stabilizing agent such as an antioxidant, for example ascorbic acid, and like known excipients. The biologically labile ester may also be formulated in aqueous solutions or suspensions for pediatric or geriatric use. Such suspensions may contain a suspending agent, a flavoring agent, a thixotropic agent, as well as a sweetening agent.

Examples of the foregoing formulations of the invention include sodium 7$\beta$-[2-(2-aminothiazol-4-yl)-2-(Z)-methoxyiminoacetamido]-3-methylsulfonyl-1-carba(dethia)-3-cephem-4-carboxylate, 1 g, as a dry powder in a 10 ml rubber-stoppered vial. Prior to administration the sodium salt of the antibiotic is dissolved in the vial in a suitable physiological diluent. An example of an oral formulation of the invention comprises 500 mg of pivaloyloxymethyl 7$\beta$-[2-(2-amino-thiazol-4-yl)-2-(Z)-methoxyiminoacetamido]-3-cyclopropylsulfonyl-1-carba(dethia)-3-cephem-4-carboxylate in a gelatin capsule.

The following examples are provided to further illustrate the present invention and are not to be construed as limiting thereof.

PREPARATION 1

Diphenylmethyl 7$\beta$-[2-t-butyloxycarbonylaminothiazol-4-yl)-2-(Z)-methoxyiminoacetamido]-3-trifluoromethylsulfonyloxy-1-carba(1-dethia)-3-cephem-4-carboxylate A. Preparation of 7$\beta$-phenoxyacetylamino-3-trifluoromethylsulfonyloxy-1-carba(1-dethia)-3-cephem-4-carboxylic acid p-Nitrobenzyl 7$\beta$-phenoxyacetylamino-3-trifluoromethylsulfonyloxy-1-carba(1-dethia)-3-cephem-4-carboxylate (20 g) was dissolved in a mixture of 200 ml of 1N HCl, 200 ml of DMF and 400 ml of THF. Zinc (4 g) was added at room temperature to the solution with stirring. After one hour, 2 g more of zinc were added and the mixture stirred for 3 hours at room temperature. The mixture was diluted with ethyl acetate and washed three times with aqueous HCl, water and brine, dried over sodium sulfate and evaporated to dryness. The product A, 15.07 g, was obtained.

B. Diphenylmethyl 7$\beta$-phenoxyacetylamino-3-trifluoromethylsulfonyloxy-1-carba(1-dethia)-3-cephem-4-carboxylate A solution of 21.62 of 1A prepared as described above in 300 ml of acetontrile was maintained under nitrogen and 9 g of diphenyldiazomethane were added portionwise at room temperature. After 2 hours, acetic acid was added to remove the color of the reaction mixture and 100 ml of toluene were added. The mixture was evaporated to dryness under vacuum and the residue chromatographed over silica using 60-40 hexanethyl acetate. The ester product B, 22.1 g, was obtained.

C. Diphenylmethyl 7$\beta$-amino-3-trifluoromethylsulfonyloxy-1-carba(1-dethia)-3-cephem-4-carboxylate A solution of 22.1 g of 1B in 300 ml of methylene chloride was cooled in an ice-ethanol bath and 3.4 ml of pyridine and 8.0 g of phosphorus pentachloride were added. After stirring for about 2 hours, the cold solution was added to a solution of 300 ml of isobutyl alcohol in 300 ml of methylene chloride cooled to $-20°$ C. After stirring for 30 minutes, 400 ml of water were added to the reaction mixture and, after stirring for 30 minutes, the mixture was extracted three times with methylene chloride. The extracts were combined and washed three times with aqueous sodium bicarbonate solution, water and brine, dried over sodium sulfate and evaporated under vacuum to a volume of 100 ml. The concentrate contained 1C which was not isolated but used in the following acylation to provide the title compound.

A solution of 10.6 g 2-(2-t-butyloxycarbonylaminothiazol-4-yl)-2-(Z)-methoxyiminoacetic acid in 100 ml of methylene chloride was treated with 3.84 ml of N-methylmorpholine, cooled in an ice bath and next treated with 6.2 g of 2-chloro-4,6-dimethoxy-s-triazine. The mixture was stirred at room temperature for 30 minutes and cooled in an ice-ethanol bath. The 100 ml solution of 1C, prepared as described above, was added to the cold solution of the acid chloride and the mixture was stirred at room temperature over two days. The reaction mixture was evaporated to dryness under vacuum and the residue dissolved in ethyl acetate. The solution was washed three times with 1N HCl, once with water, three times with aqueous sodium bicarbonate and once with brine, was dried over sodium sulfate, and chromatographed twice over sodium sulfate, and chromatographed twice over silica gel using 60% hexane in ethyl acetate. There was obtained 3.67 g of the title compound.

PREPARATION 2

Allyl 7$\beta$-[2-(2-allyloxycarbonylaminothiazol-4-yl)-2-(Z)-methoxyiminoacetamido]-3-trifluoromethylsulfonyloxy-1-carba(1-dethia)-3-cephem-4-carboxylate A. Allyl 7$\beta$2 -amino-3-trifluoromethylsulfonyloxy-1-carba(dethia)-3-cephem-4-carboxylate To a suspension of 4.30 g (9.26 mM) of 7$\beta$-phenoxyacetylamino-3-trifluoromethylsulfonyloxy-1-carba(dethia)-3-cephem-4-carboxylic acid in 270 ml of saturated aqueous sodium bicarbonate solution were added 3.22 g (9.5 mM) of tetra-n-butylammonium sulfate. The mixture was extracted three times with 100-ml portions of methylene chloride. The extracts were combined, dried over sodium sulfate and evaporated to dryness under vacuum to provide 5.50 g of the tetra n-butylammonium salt as a foam. The salt was dissolved in 35 ml of acetonitrile under nitrogen and 708 $\mu$l (8.18 mM) of allyl bromide were added to the solution. After the reaction mixture was allowed to sit at room temperature for two days, the mixture was poured into water and extracted with methylene chloride. The extract was dried over sodium sulfate and evaporated to dryness under vacuum yielding 4.0 g of crude allyl ester. The crude ester was purified by flash chromatography on a 50 mm×5.5 inch column of silica gel using 50% ethyl acetate-hexane, v:v, for elution.

The ester (0.80 g, 1.59 mM) was dissolved in 16 ml of anhydrous methylene chloride under $N_2$ and 158 μl (1.95 mM) of pyridine and 375 mg (1.80 mM) of phosphorus pentachloride were added with stirring. The mixture was stirred at room temperature for 1.5 h. When a thin layer chromatogram indicated the presence of some remaining starting material after an aliquot was treated with methanol, an additional 0.52 μl of pyridine and 125 mg of phosphorus pentachloride were added to the reaction mixture. The reaction was allowed to continue for 30 minutes and was then added via syringe to a solution of 1.47 ml (15.9 mM) of isobutanol in 65 ml of methylene chloride maintained under $N_2$ at −10° C. The cold mixture was stirred for 1 h as the temperature increased to 0° C. Water (40 ml) was added and the mixture stirred vigorously at room temperature for 15 minutes. The organic layer was separated and extracted three times with 1N HCl. The pH of the aqueous acid extract was adjusted to 7.5 with sodium bicarbonate and extracted three times with methylene chloride. The extract was dried over sodium sulfate and evaporated to dryness under vacuum to provide 0.49 g of A as a clear oil. The product ester A was used immediately in the following acylation.

B. Acylation of A

To a suspension of 456 mg (1.60 mM) of 2-(2-allyloxycarbonylaminothiazol-4-yl)-2-(Z)-methoxyiminoacetic acid in 11.2 ml of anhydrous methylene chloride maintained under $N_2$ at 0° C. were added 281 mg (1.60 mM) of chlorodimethoxytriazine and 176 μl (1.60 mM) of N-methylmorpholine. The mixture was stirred at 0° C. for about 2 h before a solution of 0.49 g (1.32 mM) of allyl 7β-amino-3-trifluoromethylsulfonyloxy-1-carba(-dethia)-3-cephem-4-carboxylate in 5 ml of anhydrous methylene chloride was added. The reaction mixture was stirred for about 14 h at room temperature, was diluted with methylene chloride, washed twice with 0.1N HCl, once with saturated aqueous sodium bicarbonate and was dried over sodium sulfate and evaporated under vacuum yielding 740 mg of the title compound as a yellow foam. The product was purified by flash chromatography over a 20 mm×5.5 inch column of silica gel with 250 ml of 50% ethyl acetate-hexane, v:v.

EXAMPLE 1

7β-[2-(2-Aminothiazol-4-yl)-2-(Z)-methoxyiminoacetamido]-3-methylsulfonyl-1-carba(1-dethia)-3-cephem-4-carboxylic acid Sodium methyl sulfinate (17 mg, 0.16 mM) was dried in a small vial via azeotropic distillation with acetonitrile and then maintained under $N_2$. Dry dimethylformamide (320 μl) and 50 mg (0.78 mM) of allyl 7β-[2-(2-allyloxycarbonylaminothiazole-4-yl)-2-(Z)-methoxyiminoacetamido]- 3-trifluoromethylsulfonyloxy-1-carba(dethia)-3-cephem-4-carboxylate, prepared as described by Preparation 2, were added to the vial. The mixture was stirred for 3 h, diluted with 1 ml of ethyl acetate and washed with water. The aqueous wash was extracted with ethyl acetate and the extract combined with the washed reaction mixture. The mixture was filtered through sodium sulfate and evaporated to dryness under vacuum yielding 52 mg of the crude di-blocked 3-methylsulfonyl product as a brown oil. The product was flash chromatographed over a 10 mm×6.5 inch silica gel column with 100 ml of 75% ethyl acetate: hexane, v:v, and yielded 33 mg of the product.

To a solution of 130 mg (0.229 mM) of the above diallyl protected 3-triflate ester prepared in additional runs as described above in 1.4 ml of acetonitrile containing 0.92 ml of diethyl ether maintained under $N_2$ were added 6.0 mg (0.024 mM) of palladium acetate and 48 mg (0.184 mM) of triphenylphosphine and the mixture was stirred at room temperature under $N_2$ for 20 minutes. The reaction mixture was cooled to 0° C. and 128 μl (0.477 mM) of tri-(n-butyl)tin hydride was added. The cooling bath was removed and the mixture was stirred at room temperature for one hour. Concentrated HCl (39.4 μl, 0.477 mM) was added to the mixture and a brown precipitate formed. The mixture was diluted with diethyl ether and the precipitate separated by centrifugation. The precipitate was washed twice with diethyl ether and the washes and precipitate were dissolved in hot 1:1, v:v, isopropanol: acetonitrile. The solution was filtered to remove the dark-brown solid. The filtrate was diluted with diethyl ether and the precipitate separated by centrifugation yielding 75 mg of the title compound. The product was purified via reverse phase $C_{18}$ HPLC using 5% acetonitrile:1% acetic acid:water, v:v:v.

The product has the following spectral characteristics:

UV ($C_2H_5OH$): 268 nm (ε=15,106), 230 nm (ε=16,836)

IR (KBr): β-lactam carbonyl, 1779 cm$^{-1}$

Mass Spectrum (FD): M+1 (444); 399; 303

NMR (DMSO, TMS, 300 MHz): 1.6 (M, 1H), 2.0 (m, 1H), 2.4 (m, 1H), 2.7 (m, 1H), 3.10 (s, 3H), 3.85 (s, 3H), 3.9–4.0 (m, 1H), 5.55 (d of d, 1H), 6.76 (s, 1H), 7.20 (br s, 2H), 7.8 (m, 2H), 9.32 (d, 1H).

The following compounds (examples 2–5) were obtained with the diallyl protected 3-triflate of Preparation 2 by following the displacement reaction conditions and the deblocking reaction conditions described by Example 1.

EXAMPLE 2

7β-[2-(2-Aminothiazol-4-yl)-2-(Z)-methoxyiminoacetamido]-3-ethylsulfonyl-1-carba-(1-dethia)-3-cephem-4-carboxylic acid UV ($C_2H_5OH$, 0.205 mg/10 ml, 1 cm path): 268 nm (ε=16,320), 230 nm (ε=18,568)

Mass Spectrum (FD): M-44 (15%), M-154 (100%).

IR (KBr disc): β-lactam 1780 cm$^{-1}$

NMR (DMSO-d$_6$, 300 MHz): δ9.33 (1H, d, 8 Hz), 7.20 (2H, br s), 6.76 (1H, s), 5.65 (1H, d of d, 8 Hz, 5 Hz), 3.90–4.00 (1H, m), 3.84 (3H, s), 3.20 (2H, d of q), 2.6–2.7 (br d of d, 1H), 2.35–2.5 (1H, br m), 1.9–2.0 (1H, br m), 1.6–1.7 (1H, d of q), 1.18 (3H, t, 8 Hz).

EXAMPLE 3

7β-[2-(2-Aminothiazol-4-yl)-2-(Z)-methoxyiminoacetamido]-3-isopropylsulfonyl-1-carba(1-dethia)-3-cephem-4-carboxylic acid UV ($C_2H_5OH$, 0.195 mg/10 ml, 1 cm path): 268 nm (ε=13,654), 237 nm (ε=12,676)

Mass Spectrum (FAB): 494 (M+Na, 50%), 472 (M+H, 15%), 177 (M-294, 50%), 155 (M-316, 50%), 119 (M-352, 100%).

IR (KBr disc): β-lactam 1772 cm$^{-1}$

NMR (DMSO-d$_6$, 300 MHz): 9.30 (1H, d, 9 Hz), 7.18 (2H, br s), 6.74 (1H, s) 5.39 (1H, d of d, 6 Hz, 9 Hz), 4.1–4.2 (br m, 1H), 3.83 (3H, s), 2.2–2.4 (2H, br m), 1.7–1.9 (1H, br m), 1.5–1.7 (1H, br m), 1.14 (3H, d), 1.11 (3H, d).

EXAMPLE 4

7β-[2-(2-Aminothiazol-4-yl)-2-(Z)-methoxyiminoacetamido]-3-phenylsulfonyl-1-carba(1-dethia)-3-cephem-4-carboxylic acid UV (C$_2$H$_5$OH, 0.200 mg/10 ml, 1 cm path): 284 nm (ε=19,746), 225 nm (ε=18,678)

MS (FAB): 506 (M+1, 25%), 309 (M-296, 20%), 155 (M-350, 80%), 119 (M-386, 100%).

NMR (DMSO-d$_6$, 300 MHz): 9.23 (1H, br, d, 8 Hz), 8.17 (2H, br d), 7.5–7.7 (3H, m), 7.2 (1H, br s), 7.18 (2H, br s), 6.70 (1H, s), 5.39 (1H, d of d), 3.78 (3H, s), 2.1–2.3 (2H, m), 1.75–1.85 (1H, m), 1.28–1.22 (1H, m).

EXAMPLE 5

7β-[2-(2-Aminothiazol-4-yl)-2-(Z)-methoxyiminoacetamido]-3-(2-thienylsulfonyl-1-carba(1-dethia)-3-cephem-4-carboxylic acid UV (C$_2$H$_5$OH, 0.197 mg/10 ml, 1 cm path): 288 nm (ε=20,116), 237 nm (ε=21,963)

Mass Spectrum (FAB): 512 (M+H, 80%), 309 (M-202, 50%), 152 (M-359, 50%), 135 (M-376, 80%), 119 (M-392, 100%).

IR (KBr disc): β-lactam 1779 cm$^{-1}$

EXAMPLE 6

7β-[2-(2-Aminothiazol-4-yl)-2-(Z)-methoxyiminoacetamido]-3-n-propylsulfonyl-1-carba(1-dethia)-3-cephem-4-carboxylic acid To a solution of 200 mg of the t-BOC-protected diphenylmethyl ester intermediate, obtained by the method of Preparation 1 above, in 2 ml of acetonitrile were added 100 mg of sodium n-propylsulfinate and the mixture was stirred at room temperature for about 12 hours. The solution was evaporated to remove the acetonitrile. DMF was added and the mixture was stirred for 2 hours. The DMF was partially removed by evaporation under vacuum and the concentrate diluted with ethyl acetate. The solution was washed four times with water and three times with 1N HCl, dried over sodium sulfate and evaporated under vacuum. The residue containing the diprotected displacement product, diphenylmethyl 7β-[2-(2-t-butyloxycarbonylaminothiazol-4-yl)-2-(Z)-methoxyiminoacetamido]-3-(n-propylsulfonyl)-1-carba(1-dethia)-3-cephem-4-carboxylate, was chromatographed over silica gel using 50/50 hexane/ethyl acetate. There were obtained 107 mg of the diblocked displacement product.

The above product, 107 mg, was dissolved in 2 ml of methylene chloride and the solution treated with 0.1 ml of triethylsilane. The mixture was cooled in an ice bath and 1 ml of trifluoroacetic acid was added. The ice bath was removed after 10 minutes and the mixture stirred for 5 hours at room temperature. The mixture was diluted with acetonitrile and evaporated to dryness under vacuum. The residue was diluted with toluene and the solution evaporated to dryness under vacuum. The residue of product was chromatographed over HP20SS using 20% acetonitrile in water. There were obtained 18.9 mg of the title compound having the following physical characteristics.

UV (C$_2$H$_5$OH): 269 nm (β=13,800), 237 nm (ε=12,600)

Mass Spectrum (FAB): M+H (472), M+Na (494).

IR (KBr): β-lactam 1773 cm$^{-1}$

NMR (DMSO-d$_6$, 300 MHz): 0.95 (3H, t), 3.7–3.8 (1H, m), 3.82 (3H, s), 5.38 (1H, d of d), 6.75 (1H, s), 7.2 (2H, br s), 9.3 (1H, br d).

EXAMPLE 7

7β-[2-(2-Aminothiazol-4-yl)-2-(Z)-methoxyiminoacetamido]-3-(3-pyridylsulfonyl-1-carba(1-dethia)-3-cephem-4-carboxylic acid To a solution of 200 mg of the t-BOC-protected diphenylmethyl ester intermediate (Preparation 1) in 4 ml of DMF were added 75 mg of sodium 3-pyridylsulfinate and the solution was stirred at room temperature for six days. The solution was diluted with 2 ml of ethyl acetate and was washed three times with water, three times with 1N HCl and brine. The solution was flash chromatographed over silica gel to provide 111 mg of t-BOC-protected 3-(3-pyridylsulfonyl) substituted diphenylmethyl ester intermediate.

The ester intermediate was deblocked and deesterified as follows. The ester 111 mg was dissolved in 2 ml of methylene chloride and 0.1 ml of triethylsilane was added followed by the addition of 1 ml of trifluoroacetic acid at ice bath temperature. Following addition, the reaction mixture was allowed to warm to room temperature and was stirred for 5 hours. The solution was treated with acetonitrile and concentrated to 2 ml. The same treatment and evaporation was repeated with acetonitrile and toluene being used. The latter solution was evaporated to dryness under vacuum and the residue chromatographed over silica gel using 2% to 20% acetonitrile-water, providing 29.3 mg of the title compound having the following physical characteristics.

UV (C$_2$H$_5$OH): 435 nm (ε=113), 288 nm (ε=11,200), 235 nm (ε=11,300)

IR (KBr): β-lactam 1774 cm$^{-1}$

Mass Spectrum (FAB): 363 (M$^+$-HSO$_2$-pyridyl)

NMR (DMSO-d$_6$, 300 MHz): 5.4 (1H, d of d), 6.7 (1H, s), 7.2 (2H, br s), 7.6 (1H, d of d), 8.4 (1H, m), 8.6 (2H, m), 8.8 (1H, br d), 9.1 (1H, br s), 9.25 (2H, d of d).

EXAMPLE 8

7β-[2-(2-Aminothiazol-4-yl)-2-(Z)-methoxyiminoacetamido]-3-(3,5-dimethylisoxazol-4-ylsulfonyl)-1-carba(1-dethia)-3-cephem-4-carboxylic acid To a solution of 200 mg of the allyloxy-carbonyl-protected allyl ester intermediate (Preparation 2) in 10 ml of acetonitrile were added 200 mg of sodium 3,5-dimethylisoxazol-4-ylsulfinate and the solution was stirred at room temperature for about 12 hours. When thin layer chromatography of the mixture showed the presence of starting material, 100 ml of 18-crown-6 ether were added and the mixture was stirred for another 12 hours at room temperature. When starting material was still detected, the mixture was warmed to 50° C. for 4 hours. Thereafter, the reaction mixture was evaporated to dryness and the residue extracted from salt water with ethyl acetate. The extract was flushed through silica gel to provide 177 mg of the allyloxycarbonyl-protected allyl ester displacement product.

The allyloxycarbonyl amino-protecting group and the allyl ester group are removed as described in Example 1 to provide the title compound.

EXAMPLE 9

The compound prepared as described by Example 8 is also obtained with the t-BOC-protected diphenylmethyl ester intermediate (Preparation 1).

From 200 mg of the intermediate (Preparation 1) and 75 mg of sodium 3,5-dimethylisoxazol-4-ylsulfinate in 4 ml of DMF, there were obtained 175 mg of the t-BOC-protected 3-(3,5-dimethylisoxazol-4-ylsulfonyl) substituted diphenylmethyl ester.

The 175 mg of the substituted ester were deblocked as before using triethylsilane and trifluoroacetic acid to provide 69.8 g of the title compound.

IR (KBr disc): β-lactam 1782 cm$^{-1}$

Mass Spectrum (FAB): M+1 (525, 15%), M-215 (309, 15%), M-369 (155, 55%), M-404 (120, 100%).

NMR (DMSO-$d_6$, 300 MHz): 9.25 (1H, d, 8 Hz), 7.2 (2H, br s), 6.76 (s, 1H), 5.5 (1H, br d of d), 3.95 (1H, br m), 3.83 (3H, s), 2.62 (3H, s), 2.46 (1H, br m), 2.33 (3H, s), 2.18-2.3 (1H, m), 1.9 (1H, m), 1.6 (1H, m).

EXAMPLE 10

7β-[2-(2-Aminothiazol-4-yl)-2-(Z)-methoxyiminoacetamido]-3-cyclopropylsulfonyl-1-carba(1-dethia)-3-cephem-4-carboxylic acid By following the procedures of Example 6, 200 mg of the intermediate triflate (Preparation 1) was reacted in 2 ml of acetonitrile with 30 mg of lithium cyclopropylsulfinate to provide 129 mg of diphenylmethyl 7β-[2-(2-t-butyloxycarbonylaminothiazol-4-yl)-2-(Z)-methoxyiminoacetamido]-3-cyclopropylsulfonyl-1-carba(1-dethia)-3-cephem-4-carboxylate.

The above ester (124 mg) was treated with triethylsilane and trifluoroacetic acid to provide, after chromatography over silica gel using ethyl acetate:acetonitrile:isopropanol:acetic acid–75:20:–4.50.5% v:v, 31 mg of the title compound which was obtained crystalline from hot acetonitrile.

UV ($C_2H_5OH$, 0.193 mg/10 ml, 1 cm path): 269 nm ($\epsilon$=19822), 237 nm ($\epsilon$=16959)

Mass Spectrum (FAB): 470 (M+1, 40%), 309 (M-160, 15%), 155 (M-314, 70%), 119 (M-350, 100%).

IR (KBr disc): β-lactam 1782 cm$^{-1}$

NMR (DMSO-$d_6$, 300 MHz): 9.32 (1H, d, 9 Hz), 7.10 (2H, br s), 6.76 (1H, s), 5.52 (1H, d of d, 6 Hz, 9 Hz), 3.9-4.0 (1H, m), 3.86 (3H, s), 2.9 (1H, br s) 2.6 (1H, br d), 2.4-2.5 (1H, m), 1.9 (1H, br m), 1.6-1.7 (1H, m).

EXAMPLE 11

7β-Phenoxyacetylamino-3-methylsulfonyl-1-carba(-dethia)-3-cephem-4-carboxylic acid To a solution of 600 mg (1.00 mM) of p-nitrobenzyl 7β-phenoxyacetylamino-3-trifluoromethylsulfonyloxy-1-carba(dethia)-3-cephem-4-carboxylate in 10 ml of acetonitrile and 2 ml of dimethylformamide under $N_2$ were added 108 mg (1.06 mM) of sodium methylsulfinate and the mixture was stirred at room temperature under $N_2$ for 16 h. The mixture was poured into ethyl acetate and the solution washed with water and brine, dried over magnesium sulfate and evaporated under vacuum yielding 0.82 g of the 3-methylsulfonyl p-nitrobenzyl ester product. The product was chromatographed over 6 inch×30 mm silica gel column with ethyl acetate yielding 0.47 (89%) of the purified product.

The product was deesterified as follows: The product ester 0.49 g (0.89 mM) was dissolved in 13 ml of DMF, 13 ml of THF and 13 ml of 1N HCl. The solution was chilled to 0° C. and 0.40 g of powdered zinc were added in two portions. After stirring in the cold, the mixture was poured into 175 ml of ethyl acetate and the solution was washed twice with 1N HCl. The colorless ethyl acetate layer was dried over magnesium sulfate and evaporated to dryness under vacuum to provide the title compound as a yellow oil. The oil crystallized on standing to provide 265 mg (75% yield).

UV ($C_2H_5OH$): 269 nm ($\epsilon$=12,908)

Percent Elemental Analysis Calculated for $C_{17}H_{18}N_2O_7S$/1 DMF:

Theory: C, 51.38; H, 5.39; N, 8.99
Found: C, 50.79; H, 5.25; N, 8.62

IR ($CHCl_3$): β-lactam carbonyl, 1780 cm$^{-1}$

Mass Spectrum (FD): M+1 (395), M (394)

NMR (DMSO, TMS, 300 MHz): 1.8 (m, 2H), 2.4 (m, 1H), 2.6-2.7 (m, 1H), 2.72 (s, 3H), 2.90 (s, 3H), 3.10 (s, 3H), 3.91 (m, 1H), 4.59 (s, 2H), 5.53 (d of d, 1H), 6.95 (m, 3H), 7.32 (t, 3H), 7.96 (s, 1H), 9.05 (d, 1H).

EXAMPLE 12

7β-(D-Phenylglycylamino)-3-methylsulfonyl-1-carba(dethia)-3-cephem-4-carboxylic acid trifluoroacetate A. Allyl 7β-[α-(t-butyloxycarbonylamino)-phenylacetylamino]-3-trifluoromethylsulfonyloxy-1-carba(dethia)-3-cephem-4-carboxylate A solution of 1.005 g (4.0 mM) of t-butyloxycarbonyl protected D-phenylglycine, 702 mg (4.0 mM) of chlorodimethoxytriazine and 440 μl (4.0 mM) of N-methylmorpholine in 28.6 ml of anhydrous methylene chloride was stirred under $N_2$ for 2 h at 0° C. A solution of allyl 7β-amino-3-trifluoromethylsulfonyloxy-1-carba(dethia)-3-cephem-4-carboxylate in 14 ml of methylene chloride was added to the cold solution and the reaction mixture was allowed to warm to room temperature and was stirred for two days. The mixture was diluted with methylene chloride, extracted with 0.1N HCl and with saturated aqueous sodium bicarbonate, was dried over magnesium sulfate and evaporated to dryness under vacuum. The crude acylation product was flash chromatographed over silica gel with 35% ethyl acetate-hexane yielding 513 mg of A.

B. Allyl 7β-[α-(t-butyloxycarbonylamino)phenylacetylamino]-3-methylsulfonyl-1-carba(dethia)-3-cephem-4-carboxylate Product A, 513 mg (0.850 mM), was dissolved in 900 μl of anhydrous DMB under $N_2$. To the solution was added about 100 mg (1 mM) of dry sodium methylsulfinate (dried by azeotropic removal of water with acetonitrile) and the mixture stirred 15 h at room temperature. The reaction mixture was diluted with ethyl acetate and washed with water. The washes were extracted with ethyl acetate and the extract combined with the reaction mixture and dried over magnesium sulfate. Flash chromatography of the dried reaction mixture over 30 mm×5.5 inch silica gel column with 50% ethyl acetate-hexane (500 ml) followed by 75% ethyl acetate-hexane (300 ml) provided 350 mg (77% yield) of B.

C. 7β-[D-α-(t-Butyloxycarbonylamino)-phenylacetylamino]-3-methylsulfonyl-1-carba(dethia))-3-cephem-4-carboxylic acid Product B, 350 mg (0.66 mM) was dissolved in 4 ml of acetonitrile and 2.6 ml of diethyl ether under $N_2$ and 16.2 mg of palladium (II) acetate and 138 mg (0.528 mM) of triphenylphosphine were added. The reaction mixture was stirred at room temperature for 20 minutes, was colled to 0° C. and 186 μl (0.69 mM) of tri-(n-butyl)tin hydride were added. The cooling bath was removed and the mixture was stirred for one hour at room temperature as the mixture became increasingly cloudy and green. The mixture was treated with 57 μl (0.69 mM) of concentrated HCl and was diluted with diethyl ether. The product formed as a gummy precipitate and the solvents were evaporated off yielding 239 mg (73%) of C.

D. Title Compound

Product C, 50 mg (0.10 mM) was dissolved in 1.0 ml of anhydrous methylene chloride, the solution cooled to 0° C., and 1 ml of trifluoroacetic acid was added. The solution was kept at 0° C. for about 45 minutes, acetonitrile added, and was then evaporated under vacuum to remove the solvents. Acetonitrile was added to the residue and evaporated off under vacuum. The acetonitrile addition and evaporation was repeated twice more to provide the title compound as a yellow oil. The oil was dissolved in about 4 ml of methanol and after standing at room temperature, the crystalline trifluoroacetate salt (title compound) was separated by centrifugation. The crystals were washed with diethyl ether and dried yielding 12 mg of title compound.

Another batch, 189 mg (0.383 mM), of C prepared as described above was treated with trifluoroacetic acid as described above and yielding the crystalline title compound from methanol. The product exhibited the following spectral properties.

UV (0.200 mg/10 ml, $C_2H_5OH$, 1 cm path): 270 nm ($\epsilon$=15,207)

IR (KBr): β-lactam carbonyl, 1787 cm$^{-1}$

Mass Spectrum (FAB): 394 (M+, 6%), 309 (M-85, 5%), 119 (M-275, 100%)

NMR ($D_2O$, 300 MHz): 7.55–7.6 (m, 5H), 5.46 (d, 5Hz, 1H), 5.22 (s, 1H), 5.22 (s, 1H), 4.0 (d of t, 1H), 3.12 (s, 3H), 2.3–2.5 (m, 2H), 1.8 (m, 1H), 1.0–1.2 (m, 1H).

EXAMPLE 13

7β-(D-Phenylglycylamino)-3-methylthio-1-carba(dethia)-3-cephem-4-carboxylic acid sulfoxide To a solution of 1.19 g (0.198 mM) of diphenylmethyl 7β-[D-α-(t-butyloxycarbonylamino)phenylacetylamino]-3-methylthio-1-carba(dethia)-3-cephem-4-carboxylate in 30 ml of methylene chloride maintained in an ice-water bath was added in one portion with stirring 0.382 g (0.221 mM) of m-chloroperbenzoic acid. The mixture was stirred for 10 minutes, diluted with 20 ml of methylene chloride and washed sequentially with water, aqueous sodium bisulfite, and with a saturated aqueous solution of sodium bicarbonate. The washed mixture was dried over sodium sulfate, filtered, and evaporated under vacuum to a yellow solid residue. The residue was dissolved in methylene chloride and was flash chromatographed on a 20 mm×6 inch silica gel column with ethyl acetate.

The product sulfoxide, 0.174 g (0.283 mM), was dissolved in methylene chloride and cooled to 0° C. With stirring, 1.17 ml of trifluoroacetic acid was added to the cold solution in one portion followed by 0.461 ml of triethyltin hydride. The reaction mixture was chromatographed (preparative thin layer) using ethyl acetate-acetonitrile, acetic acid, water:25%-9%-7%-59% to elute the product from the base line. The eluate was evaporated under vacuum to a light yellow solid which was dissolved in the minimum volume of acetonitrile. The solution was chromatographed on a 2 mm×6 inch column of HP-2055 with a 0–20% acetonitrile gradient. The fractions containing the product were combined and lyophilized. The dried product exhibited the following spectral properties.

UV ($C_2H_5OH$): 276 nm ($\epsilon$=8280)

IR (KBr): β-lactam carbonyl 1763 cm$^{-1}$

Mass Spectrum (FAB): M+1 (378)

NMR (DMSO, 300 MHz): 1.1 (m, 1H), 1.5 (m, 1H), 2.0 (m, 1H), 2.4 (m, 1H), 3.6 (m, 1H), 4.90 (s, 1H), 5.3 (m, 1H), 7.5 (m, 5H), 9.3 (d, 1H).

EXAMPLE 14

7β-[2-(2-Aminothiazol-4-yl)-2-(Z)-methoxyiminoacetamido]-3-(N-methylpyridinium-3-ylsulfonyl)-1-carba(dethia)-3-cephem-4-carboxylic acid iodide To a solution of 0.087 g (0.113 mM) of diphenylmethyl 7β-[2-(2-t-butyloxycarbonylaminothiazol-4-yl)-2-(Z)-methoxyiminoacetamido]-3-(pyridyl-3-sulfonyl)-1-carba(dethia)-3-cephem-4-carboxylate (prepared as described by Example 7) in 1.04 ml of anhydrous DMF was added with stirring, methyl iodide (100 μl). After stirring for 3 h, the reaction mixture was heated to 50° C. and then was cooled to room temperature. When thin layer chromatography of an aliquot of the mixture showed some remaining starting material, the mixture was reheated to 50° C., cooled to room temperature and stirred for 15 h. The reaction mixture was diluted with diethyl ether with formation of an oily precipitate. The ether was decanted and fresh ether added and decanted. The oily residue crystallized as fine yellow crystals of the methiodide salt.

The methiodide salt, 0.081 g (0.103 mM) was treated with 0.546 ml of trifluoroacetic acid followed by 0.216 ml of triethyltin hydride. The mixture changed color from yellowish-orange to olive green, was cooled in an ice-water bath and stirred for 1.5 h. Toluene (10 ml) was added to the mixture which was then evaporated under vacuum to a green gum. Acetonitrile was added to the gum with formation of a light yellow precipitate. A mixture of water and acetonitrile were added to dissolve the yellow solid. The solution was evaporated to again yield the gum. The gum was dissolved in water and chromatographed over HP20SS (0 to 20% $CH_3CN$). Fractions containing the product were freeze-dried. The dried product exhibited the following spectral properties.

Mass Spectrum (FA): M (521)

NMR (DMSO, 300 MHz): 1.4 (m, 1H), 1.8 (m, 1H), 2.4 (m, 2H), 3.8 (m, 1H), 3.9 (s, 3H), 4.35 (s, 3H), 5.35 (d of d, 1H), 7.0 (s, 1H), 8.2 (t, 1H), 9.0 (m, 2H), 9.4 (d, 1H), 9.6 (s, 1H).

I claim:

1. The compound of the formula

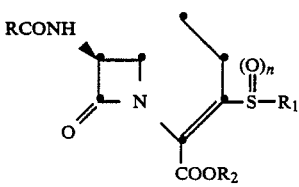

wherein R is hydrogen; $C_1$–$C_6$ alkyl; $C_1$–$C_6$ alkyl substituted by cyano, carboxy, halogen, amino, $C_1$–$C_4$ alkoxy, $C_1$–$C_4$ alkylthio, or trifluoromethylthio; phenyl or a substituted phenyl group of the formula

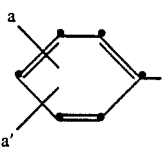

wherein a and a' independently are hydrogen, halogen, hydroxy, $C_1$-$C_4$ alkoxy, $C_1$-$C_4$ alkanoyloxy, $C_1$-$C_4$ alkyl, $C_1$-$C_4$ alkylthio, amino, $C_1$-$C_4$ alkanoylamino, $C_1$-$C_4$ alkylsulfonylamino, carboxy, carbamoyl, aminosulfonyl, hydroxymethyl, aminomethyl, or carboxymethyl;
a group of the formula

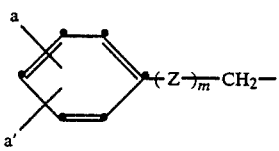

wherein a and a' have the same meanings as defined above, Z is O or S, and m is 0 or 1;
a heteroarylmethyl group of the formula

wherein $R^1$ is thienyl, furyl, benzothienyl, benzofuryl, pyridyl, 4-pyridylthio, pyrimidyl, pyridazinyl, indolyl, pyrazolyl, imidazolyl, triazolyl, tetrazolyl, oxazolyl, isoxazolyl, thiazolyl, oxadiazolyl, thiadiazolyl, and such heteroaryl groups substituted by amino, hydroxy, halogen, $C_2$-$C_4$ alkyl, $C_1$-$C_4$ alkoxy, $C_1$-$C_4$ alkylsulfonylamino;
a substituted methyl group of the formula

wherein $R^2$ is $R^1$ as defined above, cyclohex-1,4-dienyl, a phenyl group or substituted phenyl group of the formula

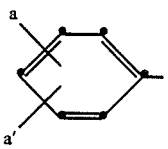

wherein a and a' have the above defined meanings, and Q is hydroxy, $C_1$-$C_4$ alkanoyloxy, carboxy, sulfo, amino, sulfoamino, a substituted amino group of the formula

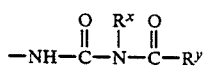

wherein $R^x$ is hydrogen or $C_1$-$C_3$ alkyl, $R^y$ is $C_1$-$C_4$ alkyl, furyl, thienyl, phenyl, halophenyl, nitrophenyl, styryl, halostyryl, nitrostyryl or a group

wherein $R^x$ is hydrogen or $C_1$-$C_3$ alkyl, and $R^z$ is hydrogen, $C_1$-$C_3$ alkylsulfonyl, $C_1$-$C_3$ alkyl, or $C_1$-$C_4$ alkanoyl; a substituted amino group of the formula

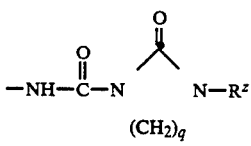

wherein $R^z$ has the same meanings as defined above and q is 2 or 3; a substituted amino group of the formula

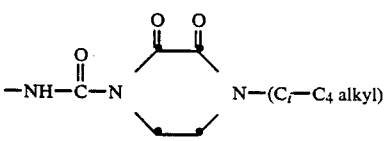

a benzamido group of the formula

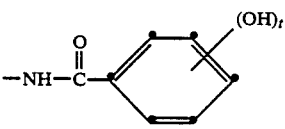

wherein t is 1 or 3; a pyridone or hydroxy-substituted pyridone group of the formula

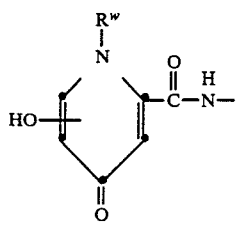

wherein $R^w$ is hydrogen or $C_1$-$C_4$ alkyl; a pyridyl group of the formula

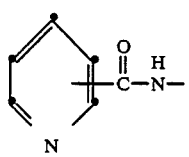

and such pyridyl group substituted by $C_1$-$C_4$ alkyl, amino, carboxy, hydroxy or halogen; an imidazoyl or pyrazolyl group of the formulae

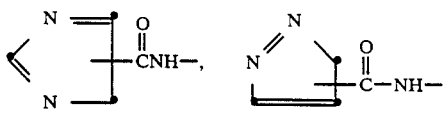

and such groups substituted by $C_1$-$C_4$ alkyl, carboxy, amino or halogen;

a benzypyridazin-4-one-3-ylcarbonylamino group of the formulae

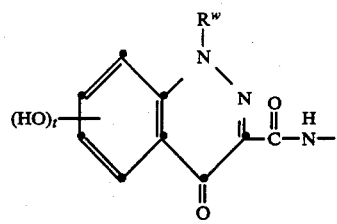

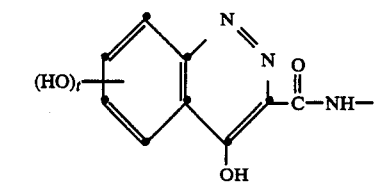

wherein $R^z$ is hydrogen or $C_1$-$C_4$ alkyl; and t is 1-3; or Q is a substituted amino group of the formula

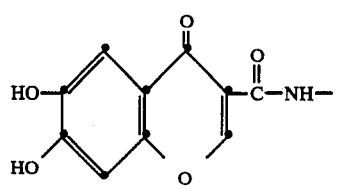

or R is a keto group or an oximino-substituted group of the formulae

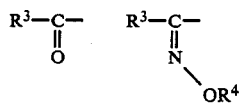

wherein $R^3$ is $R^2$ as defined above and $R^4$ is hydrogen; $C_1$-$C_4$ alkyl; $C_1$-$C_4$ alkyl substituted by halogen or amino; a substituted alkyl or cycloalkyl group of the formula

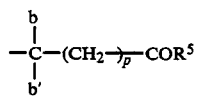

wherein b and b' independently are hydrogen, or $C_1$-$C_3$ alkyl, p is 0, 1, 2, or 3; and b and b' when taken together with the carbon to which they are bonded form a 3- to 6-membered carbocyclic ring, and $R^5$ is hydroxy, $C_1$-$C_4$ alkoxy, amino, $C_1$-$C_4$ alkylamino, or di($C_1$-$C_4$ alkyl)amino;

a cyclic lactam of the formula

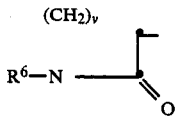

wherein v is 2, 3, or 4; and $R^6$ is hydrogen or $C_1$-$C_3$ alkyl;

or $R^4$ is a heteroarylmethyl group of the formula $R^1-CH_2-$ wherein $R^1$ has the same meanings as defined hereinabove;

n is 1 or 2;

$R_1$ is $C_1$-$C_6$ alkyl; $C_1$-$C_6$ alkyl substituted by hydroxy, $C_1$-$C_4$ alkoxy, $C_1$-$C_4$ alkylthio, trifluoromethyl, carboxy, carbamoyl, amino, $C_1$-$C_4$ alkylamino, di-($C_1$-$C_4$ alkyl)amino, halogen, cyano, phenyl, or substituted phenyl as defined above for R; $C_2$-$C_6$ alkenyl; $C_3$-$C_7$ cycloalkyl; phenyl or substituted phenyl as defined above for R; or a 5- or 6-membered heterocycle selected from thienyl, furyl, pyrryl, imidazolyl, pyrazolyl, oxazolyl, isoxazolyl, thiazolyl, isothiazolyl, oxadiazolyl, thiadiazolyl, triazolyl, tetrazolyl, pyridyl, pyrimidyl, triazinyl, or pyrazinyl; the benzheterocycles, benzothienyl, benzofuryl, indolyl, benzimidazolyl, or benztriazolyl, and said 5- or 6-membered heterocycle and said benzheterocycle substituted by $C_1$-$C_4$ alkyl, halogen, hydroxy, $C_1$-$C_4$ alkoxy, amino, carboxy, cyano, or carbamoyl; and when said heterocycle or benzheterocycle contains a basic ring nitrogen, the $C_1$-$C_4$ alkyl quaternary chloride, bromide or iodide salt thereof;

$R_2$ is hydrogen or a carboxy-protecting group, and, when $R_2$ is hydrogen, the pharmaceutically acceptable non-toxic salts thereof.

2. The compound of claim 1 wherein $R_1$ is $C_1$-$C_6$ alkyl, $C_3$-$C_7$ cycloalkyl, $C_2$-$C_6$ alkenyl, substituted $C_1$-$C_6$ alkyl, phenyl, or substituted phenyl.

3. The compound of claim 1 wherein $R_1$ is a 5- or 6-membered heterocycle.

4. The compound of claim 1 wherein R is a group of the formula

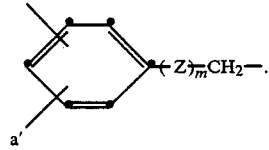

5. The compound of claim 4 wherein m is 1, Z is 0, and $R_1$ is $C_1$-$C_6$ alkyl, $C_2$-$C_6$ alkenyl, or $C_3$-$C_7$ cycloalkyl.

6. The compound of claim 5 which is 7β-phenoxyacetylamino-3-methylsulfonyl-1-carba(dethia)-3-cephem-4-carboxylic acid and the pharmaceutically acceptable salts thereof.

7. The compound of claim 1 wherein R is a heteroarylmethyl group of the formula $R^1-CH_2-$ 8. The compound of claim 7 wherein $R^1$ is 2-thienyl, 2-furyl, tetrazolyl, thiazolyl, thiadiazolyl or oxadiazolyl.

9. The compound of claim 8 wherein $R^1$ is thiazolyl or thiadiazolyl.

10. The compound of claim 1 wherein R is a substituted methyl group of the formula $$R^2-\underset{Q}{\underset{|}{CH}}-$$

wherein Q is hydroxy, $C_1$-$C_4$ alkanoyloxy, carboxy, sulfo, amino, or sulfoamino.

11. The compound of claim 10 wherein $R^2$ is phenyl or substituted phenyl and Q is hydroxy, carboxy, or amino.

12. The compound of claim 11 which is 7β-(D-phenylglycylamino)-3-methylsulfonyl-1-carba(dethia)-3-cephem-4-carboxylic acid.

13. The compound of claim 1 wherein R is an oximino-substituted group of the formula $$R^3-\underset{\underset{OR^4}{\overset{\|}{N}}}{C}-$$

14. The compound of claim 13 wherein $R^3$ is phenyl, substituted phenyl, thienyl, furyl, oxazolyl, thiazolyl, or thiadiazolyl, or said thienyl, formyl, oxazolyl, thiazolyl, or thiadiazolyl group substituted by amino, hydroxy, halogen, $C_1$-$C_4$ alkyl, $C_1$-$C_4$ alkoxy, or $C_1$-$C_4$ alkylsulfonylamino.

15. The compound of claim 14 of the formula

[structure with $R_5$, S, thiazole, CONH, β-lactam, $SO_2R_1$, COOR_2, OR^4, syn]

wherein $R_5$ is amino or protected amino, $R_4$ is $C_1$-$C_4$ alkyl, or a carboxy or protected carboxy-substituted alkyl group, and $R_2$ is hydrogen or a carboxy-protecting group.

16. The compound of claim 15 wherein $R_5$ is amino and $R_1$ is $C_1$-$C_6$ alkyl, $C_3$-$C_7$ cycloalkyl, phenyl or substituted phenyl.

17. The compound of claim 15 wherein $R_5$ is amino and $R_1$ is a 5- or 6-membered heterocycle.

18. The compound of claim 16 wherein $R_1$ is methyl, ethyl, n-propyl, or isopropyl, and $R^4$ is methyl.

19. The compound of claim 16 wherein $R_1$ is phenyl.

20. The compound of claim 17 wherein $R_1$ is 2-thienyl, 3-pyridyl, or 3,5-dimethylisoxazol-4-yl, and $R^4$ is methyl.

21. The compound of claim 17 wherein $R_1$ is 3-(N-methylpyridinium) iodide.

22. A compound of the formula

[structure with $R^o$, β-lactam, N, S(O)_n-$R_1$, COOR_2]

wherein $R^0$ is amino or protected amino;
$R_1$ is $C_1$-$C_6$ alkyl; $C_1$-$C_6$ alkyl substituted by hydroxy, $C_1$-$C_4$ alkoxy, $C_1$-$C_4$ alkylthio, trifluoromethyl, carboxy, carbamoyl, amino, $C_1$-$C_4$ alkylamino, di-($C_1$-$C_4$ alkyl)amino, halogen, cyano, phenyl or substituted phenyl of the formula

[phenyl ring with positions a and a']

wherein a and a' independently are hydrogen, halogen, hydroxy, $C_1$-$C_4$ alkoxy, $C_1$-$C_4$ alkanoyloxy, $C_1$-$C_4$ alkyl, $C_1$-$C_4$ alkylthio, amino, $C_1$-$C_4$ alkanoylamino, $C_1$-$C_4$ alkylsulfonylamino, carboxy, carbamoyl, aminosulfonyl, hydroxymethyl, aminomethyl, or carboxymethyl; $C_2$-$C_6$ alkenyl; $C_3$-$C_7$ cycloalkyl; phenyl or substituted phenyl as defined above; or a 5- or 6-membered heterocycle selected from thienyl, furyl, pyrryl, imidazolyl, pyrazolyl, oxazolyl, isoxazolyl, thiazolyl, isothiazolyl, oxadiazolyl, thiadiazolyl, triazolyl, tetrazolyl, pyridyl, pyrimidyl, triazinyl, or pyrazinyl; the benzheterocycles, benzothienyl, benzofuryl, indolyl, benzimidazolyl, or benztriazolyl, and said 5- or 6-membered heterocycle and said benzheterocycle substituted by $C_1$-$C_4$ alkyl, halogen, hydroxy, $C_1$-$C_4$ alkoxy, amino, carboxy, cyano, or carbamoyl; and when said heterocycle or benzheterocycle contains a basic ring nitrogen, the $C_1$-$C_4$ alkyl quaternary chloride, bromide or iodide salt thereof; $R_2$ is hydrogen or a carboxy-protecting group; and n is 1 or 2.
$R_2$ is hydrogen, a carboxy-protecting group, or a group forming a biologically labile ester and, when $R_2$ is hydrogen, the pharmaceutically acceptable non-toxic salts thereof; are antibiotics useful in the treatment of infectious disease.

23. The compound of claim 22 wherein $R^0$ is amino.

24. The compound of claim 22 wherein $R^0$ is a protected amino group.

25. The compound of claim 22 wherein n is 2 and $R_1$ is $C_1$-$C_6$ alkyl, $C_3$-$C_7$ cycloalkyl, phenyl, or substituted phenyl.

26. A method for treatment of bacterial infections in man and animals which comprises administering to said host an antibacterially effective amount of a compound of claim 1 wherein $R_2$ is hydrogen or a pharmaceutically acceptable, non-toxic salt thereof.

27. The method of claim 26 where, in said compound, R is an oximino-substituted group of the formula $$R^3-\underset{\underset{OR^4}{\overset{\|}{N}}}{C}-$$

wherein $R^3$ is the 2-aminothiazol-4-yl group and $R^4$ is $C_1$-$C_4$ alkyl.

28. The method of claim 27 where in said compound $R^4$ is methyl; $R_1$ is $C_1$-$C_6$ alkyl, $C_3$-$C_7$ cycloalkyl, phenyl, or substituted phenyl.

* * * * *